US011968974B2

(12) United States Patent
Bacchetta et al.

(10) Patent No.: US 11,968,974 B2
(45) Date of Patent: Apr. 30, 2024

(54) CROSS-CIRCULATION PLATFORM FOR RECOVERY, REGENERATION, AND MAINTENANCE OF EXTRACORPOREAL ORGANS

(71) Applicant: The Trustees of Columbia University in the City of New York, New York, NY (US)

(72) Inventors: Matthew Bacchetta, Tenafly, NJ (US); Scott Chicotka, New York, NY (US); Kenmond Fung, New York, NY (US); Brandon Guenthart, New York, NY (US); John O'Neill, New York, NY (US); Gordana Vunjak-Novakovic, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1072 days.

(21) Appl. No.: 16/244,283

(22) Filed: Jan. 10, 2019

(65) Prior Publication Data
US 2019/0141985 A1 May 16, 2019

Related U.S. Application Data

(63) Continuation of application No. PCT/US2017/041990, filed on Jul. 13, 2017.
(Continued)

(51) Int. Cl.
*C12M 3/00* (2006.01)
*A01N 1/00* (2006.01)
(Continued)

(52) U.S. Cl.
CPC ............... *A01N 1/021* (2013.01); *A01N 1/02* (2013.01); *A01N 1/0247* (2013.01); *A61J 1/00* (2013.01);
(Continued)

(58) Field of Classification Search
CPC .................. A01N 1/0247; A01N 1/021
See application file for complete search history.

(56) References Cited

U.S. PATENT DOCUMENTS 7,410,474 B1 * 8/2008 Friend ...................... A01N 1/02
435/284.1
8,349,551 B2 * 1/2013 Owen ...................... H04L 67/02
435/1.2
(Continued)

FOREIGN PATENT DOCUMENTS

WO    1996029865    10/1996

OTHER PUBLICATIONS

Norman, J. et al. "Perfusion Techniques in Temporary Human-Isloated Ex Vivo Porcine Liver Cross Circulation" JSR, vol. VI, No. 3, pp. 121-125 (Mar. 1966).
(Continued)

*Primary Examiner* — Nathan A Bowers
(74) *Attorney, Agent, or Firm* — Amster, Rothstein & Ebenstein LLP

(57) ABSTRACT

Described are systems, methods, and devices relating to normothermic extracorporeal support of an organ, tissue, or bioengineered graft comprising cross-circulation (XC) perfusion for prolonged periods (days to weeks) via an XC perfusion circuit in connection with an extracorporeal host (e.g., animal, patient, organ transplant recipient) are disclosed. The XC perfusion circuit comprises auto-regulation of blood flow based on the trans-organ blood pressure difference between arterial and venous pressure. Recipient
(Continued)

support enabled 36 h of normothermic perfusion that maintained healthy lungs with no significant changes in physiologic parameters and allowed for the recovery of injured lungs. Extended support enabled multiscale therapeutic interventions in all extracorporeal lungs. Lungs exceeded transplantation criteria.

9 Claims, 32 Drawing Sheets

Related U.S. Application Data

(60) Provisional application No. 62/472,744, filed on Mar. 17, 2017, provisional application No. 62/361,843, filed on Jul. 13, 2016.

(51) Int. Cl.
    *A01N 1/02*     (2006.01)
    *A61J 1/00*     (2023.01)
    *A61M 1/16*     (2006.01)
    *C12M 1/00*     (2006.01)
    *C12M 1/34*     (2006.01)
    *A61M 1/36*     (2006.01)
    *A61M 1/38*     (2006.01)

(52) U.S. Cl.
    CPC .............. *A61M 1/16* (2013.01); *C12M 29/12* (2013.01); *C12M 29/14* (2013.01); *C12M 41/16* (2013.01); *A01N 1/0278* (2013.01); *A61M 1/3621* (2013.01); *A61M 1/38* (2013.01); *A61M 2210/1039* (2013.01)

(56) References Cited

U.S. PATENT DOCUMENTS

| | | | |
|---|---|---|---|
| 2005/0182349 A1* | 8/2005 | Linde | A61M 1/3489 604/4.01 |
| 2008/0017194 A1* | 1/2008 | Hassanein | A01N 1/02 128/200.24 |
| 2011/0076666 A1* | 3/2011 | Brassil | A01N 1/0247 435/284.1 |
| 2012/0330438 A1* | 12/2012 | Keshavjee | A01N 1/0247 623/23.65 |
| 2016/0120173 A1* | 5/2016 | Austen, Jr. | A01N 1/0242 600/36 |
| 2017/0015963 A1* | 1/2017 | Ott | A61K 35/42 |
| 2019/0059359 A1* | 2/2019 | Potenziano | A01N 1/021 |
| 2020/0253194 A1* | 8/2020 | Clavien | A01N 1/0247 |

OTHER PUBLICATIONS

Chen, R. et al. "Bridging With Solid-Organ Xenotransplants" (1999), Transplantation Reviews, vol. 13, No. 4, pp. 92-202 (Oct. 1999).
Abouna, G. et al. "Extracorporeal Liver Perfusion System For Successful Hepatic Support Pending Liver Regeneration or Liver Transplantation: A Pre-Clinical Controlled Trial", Transplantation, vol. 67, No. 12, pp. 1576-1583 (Jun. 27, 1999).
Levy, M. et al. "Liver Allotransplantation After Extracorporeal Heptic Support With Transgenci (hCD55/hCD59) Porcine Livers," Transplantation, vol. 69, No. 2, pp. 272-280 (Jan. 27, 2000).
O'Neill, J. et al. "Cross-circulation for extracorporeal support and recovery of the lung" Nature Biomedical Engineering, vol. 1, Article No. 0037, pp. 1-15 (Mar. 6, 2017).
Supplementary Partial European Search Report and Provisional Opinion, dated Feb. 13, 2020, European Application No. EP17828488.

\* cited by examiner

| | Circuit Elements |
|---|---|
| A | airflow probe |
| H | warm water jacket |
| IJ | internal jugular vein |
| L | leukocyte reducer |
| O | oxygenator |
| P | pressure sensor |
| PA | pulmonary artery |
| PF | plasma filter |
| PV | pulmonary vein |
| Q | flow probe |
| R | reservoir (plasma) |
| S | sample port |
| T | temperature probe |

Single lung venous cannulation

| | |
|---|---|
| B | bronchus |
| BR | biologic cuff device |
| LAC | left atrial cuff |
| LPV | left pulmonary vein |
| PA | pulmonary artery |
| PV | pulmonary vein |
| RB | right main stem bronchus |
| RPV | right pulmonary vein |
| T | trachea |

| | Circuit Elements |
|---|---|
| B | bubble detector |
| IJ | internal jugular vein |
| P | pressure sensor |
| PA | pulmonary artery |
| PF | plasma filter |
| PV | pulmonary vein |
| Q | flow probe |

CROSS-CIRCULATION PLATFORM FOR RECOVERY, REGENERATION, AND MAINTENANCE OF EXTRACORPOREAL ORGANS

CROSS-REFERENCE TO RELATED APPLICATIONS

This application is a continuation of International Application No. PCT/US2017/041990, filed on Jul. 13, 2017, which claims priority to U.S. Provisional Application No. 62/361,843, filed on Jul. 13, 2016 and U.S. Provisional Application No. 62/472,744, filed Mar. 17, 2017 which are herein incorporated by reference in their entirety.

FIELD OF THE DISCLOSED SUBJECT MATTER

This invention relates to a system, devices and methods for prolonged (days to weeks) normothermic extracorporeal support of an organ, tissue, or bioengineered graft by cross-circulation.

BACKGROUND OF THE DISCLOSED SUBJECT MATTER

Since about 1970, organ transplantation to treat terminal illnesses has become routine, although still rare. Transplants procedures for heart, lung, kidney, liver, small intestine and pancreas organs have been developed. For example, end-stage lung disease has a profound socioeconomic impact and remains the third leading cause of death worldwide. Twenty-five million Americans suffer from end-stage lung disease and 400,000 patients die every year. Lung transplantation is the only definitive treatment, but the number of transplants is limited by shortage of transplantable donor lungs. However, donor organ demand far exceeds supply, and due to stringent listing criteria, the actual demand is probably underestimated. Currently, four out of five donor lungs are deemed unacceptable for transplantation at the time of donation, making lung the least utilized solid organ and necessitating the increasing use of extracorporeal membrane oxygenation as a bridge-to-transplant for critically ill patients. In 2015 there were only 1,854 lung transplants in the U.S.A.

To address these challenges, there are major initiatives worldwide to increase the number of transplantable lungs, including the following: (1) Criteria expansion: the use of donors older than 55 years, or lungs donated following cardiac deaths; (2) Extracorporeal devices: ex vivo lung perfusion (EVLP) to recondition marginally unacceptable donor lungs; (3) Bioengineered lungs: tissue-engineering strategies utilizing stem cells and fully decellularized or bioartificial scaffolds to develop functional lungs de novo; (4) Xenogeneic lungs: genomic and immunologic alterations to enable the xenotransplantation of swine or non-human primate lungs, thereby providing a constant supply of donor organs. However, despite these efforts, the annual number of lung transplantations remains steady, and waitlist mortality continues to rise. Among current approaches, EVLP may hold the greatest promise for immediate clinical impact. The utility of commercially available EVLP systems for recovery of marginally unacceptable donor lungs is under investigation in clinical trials, and several have already employed EVLP before lung transplantation. Nevertheless, the number of lungs recovered using EVLP remains limited, and may be insufficient to meet the growing demand.

Current organ preservation techniques typically involve hypothermic storage of the organ in a chemical preservation solution on ice. These techniques utilize a variety of solutions, none of which sufficiently protect the organ from damage resulting from ischemia. Such injuries are particularly undesirable when an organ is intended to be transplanted from a donor into a recipient.

Effective physiologic preservation of an ex vivo or extracorporeal organ would provide important benefits compared to conventional approaches. For instance, physiologic ex vivo preservation would permit more careful monitoring, functional testing, assessment, and therapy of the harvested organ. This would in turn allow earlier detection and potential repair of defects in the harvested organ, further reducing the likelihood of post-transplant organ failure. The ability to perform and assess simple repairs on the organ would also allow many organs with minor defects to be saved, whereas current transplantation techniques require them to be discarded. This may be critically important when harvesting lungs because lungs are easily compromised even before harvesting within the donor's body.

In addition, more effective matching between the organ and a particular recipient may be achieved, further reducing the likelihood of eventual organ rejection. Current transplantation techniques rely mainly on matching donor and recipient blood types, which by itself is a relatively unreliable indicator of whether or not the organ will be rejected by the recipient. A more preferred test for organ compatibility is a Human Leukocyte Antigen (HLA) matching test, but current cold ischemic organ preservation approaches preclude the use of this test, which can often require 12 hours or more to complete.

Using conventional approaches, injuries caused by ischemia increase as a function of the length of time an organ is maintained ex vivo. For example, a lung may typically be preserved ex vivo for only about 6 to about 8 hours before it becomes unusable for transplantation. A heart typically may be preserved ex vivo for only about 4 to about 6 hours before it becomes unusable for transplantation. These relatively brief time periods limit the number of recipients who can be reached from a given donor site, thereby restricting the recipient pool for a harvested organ. Even within the time limits, the organs may nevertheless be significantly damaged. A significant issue is that there may not be any observable indication of the damage. Because of this, less-than-optimal organs may be transplanted, resulting in post-transplant organ dysfunction or other injuries. Thus, it would be desirable to develop techniques that can extend the time during which an organ can be preserved in a healthy state ex vivo. Such techniques would reduce the risk of post-transplant organ failure and enlarge potential donor and recipient pools.

Prolonged and reliable ex vivo organ care would also provide benefits outside the context of organ transplantation. For example, a patient's body, as a whole, can typically tolerate much lower levels of chemo-, bio- and radiation therapy than many particular organs. An ex vivo organ care system would permit an organ to be removed from the body and treated in isolation, reducing the risk of damage to other parts of the body.

Conventional extracorporeal organ support systems are closed circuits that rely on re-circulation of a perfused fluid (e.g., blood, organ preservation solution). Closed re-perfusion systems lack the ability to maintain physiologic homeostasis, resulting in the accumulation of toxic metabolites and waste products that have deleterious effects on organ function and viability. Such effects strictly limit the duration of extracorporeal organ support to approximately 12 hours—a prohibitively short duration of time to intervene (e.g., to treat infections with antibiotics, improve organ function by clearing inflammation or repairing injuries, regenerate organ with gene or cell therapies) in an extracorporeal organ or tissue. Extended duration of extracorporeal support (greater than 24 hours) allows for intervention and recovery of otherwise unusable donor organs, thereby significantly expanding the pool of transplantable donor organs, as well providing a means for modifying the donor organ.

In view of the foregoing, improved systems, methods, and devices for caring for an organ ex vivo are needed.

Notably, clinical EVLP systems are approved to support lungs for up to 6 h, a time too short for recovery of lungs beyond the marginally unacceptable range and for advanced therapeutic interventions (for example, pharmacotherapy, immunomodulation and gene/cell therapy). The physiologic limitations of EVLP can be attributed to the absence of systemic regulation (for example, renal, hepatic, pancreatic, neurohormonal). Even with repeated exchanges of perfusate, the loss of homeostasis in the extracorporeal lung inevitably leads to cellular damage, pulmonary oedema, impaired gas exchange and deterioration of lung function.

SUMMARY

In one aspect, systems, methods, and devices relating to normothermic extracorporeal support of an organ, tissue, or bioengineered graft comprising cross-circulation (XC) perfusion for prolonged periods (days to weeks) via an XC perfusion circuit in connection with an extracorporeal host (e.g., animal, patient, organ transplant recipient) are provided. The connection is made directly between the host vasculature and the extracorporeal organ, tissue, or bioengineered graft. The organs can be supported to provide fully maintained organ function, microscopic integrity, and transplantability.

In another aspect, a system for maintaining an extracorporeal organ, tissue or bioengineered graft is provided. In one embodiment, the system comprises an extracorporeal chamber to contain and support the organ, tissue or bioengineered graft; and an extracorporeal cross-circulation circuit to connect the organ, tissue or bioengineered graft with a host organism wherein the circuit comprises auto-regulation of blood flow based on the trans-organ blood pressure difference between arterial and venous pressure.

In another embodiment, the extracorporeal organ chamber comprises an organ- and/or size-specific organ-negative molded soft bladder (for containing the organ, tissue or graft, e.g., lung, heart-lung, liver, kidney, gut, limb; pediatric, adult), temperature-controlled interior maintained with recirculating temperature-controlled water in a range from 4° C. to 40° C., such as from 4° C. to 37° C.); and an articulated base for organ orientation variability.

The articulated base may allow for increased vascular recruitment and improved perfusion.

Embodiments of the chamber may further comprise one or more of the following features including time-controlled humidifier and misting spray onto the organ, integrated scale for monitoring and recording organ weight, real-time macroscopic video recording of the organ with remote monitoring capability, access ports with sterile air filter for biopsies and/or imaging, access for sterile manual interventions in chamber, and sterilizable and single-use disposable components.

The extracorporeal cross-circulation circuit preferably comprises a pressure-controlled, adjustable blood flow with organ-specific trans-organ pressure feedback to a circulating pump. The pressure in the circuit is desirably controlled to maintain optimal trans-organ vascular gradients.

Embodiments of the extracorporeal cross-circulation circuit may further comprise one or more of the following features including a re-circulation tubing jacket for warming exposed tubing, integrated heat exchanger, integrated access ports for blood sampling, and remote monitoring and control of the circulating pump.

The system may further comprise an extracorporeal organ chamber stand comprising automatic height adjustability based on feedback from extracorporeal organ in-flow and out-flow line pressures; optionally at least one organ-specific accessory such as a ventilator for oxygenating lung tissue; bile collection receptacle for a liver; urimeter for a kidney; and/or electrocardiogram monitoring or electric pacer for a heart; and a power source, preferably without the need for an electrical outlet.

The organ chamber stand includes the ability to raise and lower the organ chamber to modulate cross-circulation circuit pressures so that desirable perfusion rates are maintained.

Embodiments of the chamber stand may further comprise one or more of the following features including rechargeable power source back-up, and a mobile platform (such as a rolling cart) for normothermic organ transport from donor to recipient site.

The invention also provides a biologic cuff device with a sensor comprising a native vessel as a biological bridge to manage pulmonary venous drainage. The cuff device comprises a native aortic arch (from the donor organism) in fluid connection with at least one head vessel port accommodating a sensor to monitor a condition of the perfusion fluid (blood) within the cross circulation circuit (e.g., pressure, flow, temperature, blood chemistry).

The biologic cuff device may further comprise at least one other donor vascular component (e.g. thoracic aorta with superior mesenteric artery, inferior vena cava, portal vein, etc.) to provide a customizable system for support of a specific extracorporeal organ type.

The invention also provides a draining cannula comprising an expandable, rounded, crenelated (castle-shaped), fenestrated, or tapering tip housed in deployable sheath (c.f., a stent) for secure placement; and a plurality of periodically-spaced grooves and/or tabs for secure fastening/suturing, or a lockable external slip ring with a single tie securing mechanism.

The invention also provides a patient safety clamp for a cannula, comprising at least one sensor to monitor a condition, including at least one of air bubbles, bleeding, blood pressure, heart rate or other host vital signs including mixed venous oxygen saturation, lactate, etc., of the host organism (e.g., patient) connected to the cross circulation circuit; and automatic clamping of the host cannula to prevent air bubbles, bleeding, or significant physiologic changes in host condition. The "automatic clamping" or flow control (reduction, occlusion) is managed through a feedback circuit on pressure and flow monitors.

The subject matter described and embodied herein relates to the use the system described above, and any embodiments thereof, to maintain an extracorporeal organ, tissue, or bioengineered graft by perfusing blood from a host organism through the extracorporeal organ, tissue, or bioengineered graft via a cross circulation circuit while modulating the blood flow to maintain desired trans-organ vascular gradients; and maintaining the extracorporeal organ, tissue, or bioengineered graft within a temperature range of from 4° C.

to 40° C., such as from 4° C. to 37° C. or from 30° C. to 40° C. or from 35° C. to 40° C.; wherein the cross circulation circuit comprises auto-regulation of blood flow based on the trans-organ blood pressure difference between arterial and venous pressure.

In another aspect, provided herein is a method for normothermic extracorporeal support of an organ, tissue, or bioengineered graft, comprising obtaining an extracorporeal organ, tissue, or bioengineered graft; maintaining the extracorporeal organ, tissue, or bioengineered graft at 4° C. for a period of time; connecting to the extracorporeal organ, tissue, or bioengineered graft and to the vasculature of a host organism a cross circulation circuit comprising auto-regulation of blood flow based on the trans-organ blood pressure difference between arterial and venous pressure; perfusing blood from the host through the extracorporeal organ, tissue, or bioengineered graft via the cross circulation circuit while modulating the blood flow to maintain desired trans-organ vascular gradients; and maintaining the extracorporeal organ, tissue, or bioengineered graft within a temperature range of from 30° C. to 40° C.

Another aspect is a method for treating an extracorporeal organ, tissue, or bioengineered graft that has been subjected to maintenance at 4° C. for a period of time, the method comprising: connecting to the extracorporeal organ, tissue, or bioengineered graft and to the vasculature of a host organism a cross circulation circuit comprising auto-regulation of blood flow based on the trans-organ blood pressure difference between arterial and venous pressure; perfusing blood from the host through the extracorporeal organ, tissue, or bioengineered graft via the cross circulation circuit while modulating the blood flow to maintain desired trans-organ vascular gradients; and maintaining the extracorporeal organ, tissue, or bioengineered graft within a temperature range of from 30° C. to 40° C.

A method for normothermic extracorporeal support of an organ, tissue, or bioengineered graft, comprising obtaining an extracorporeal organ, tissue, or bioengineered graft wherein the organ, tissue, or bioengineered graft exhibits acute injury prior to treatment; or exhibits a reversible pathologic condition prior to treatment; connecting to the extracorporeal organ, tissue, or bioengineered graft and to the vasculature of a host organism a cross circulation circuit comprising auto-regulation of blood flow based on the trans-organ blood pressure difference between arterial and venous pressure; perfusing blood from the host through the extracorporeal organ, tissue, or bioengineered graft via the cross circulation circuit while modulating the blood flow to maintain desired trans-organ vascular gradients; and maintaining the extracorporeal organ, tissue, or bioengineered graft within a temperature range of from 4° C. to 40° C.

Embodiments of any of these methods include:

Methods further comprising placing the extracorporeal organ, tissue, or bioengineered graft in an extracorporeal organ chamber, such as described herein. Methods further comprising treating the extracorporeal organ, tissue, or bioengineered graft by providing at least one of an energy substrate, a circulating repair factor, metabolic clearance, or therapeutic intervention, including medication, drug nanoparticles, gene therapy, stem cell therapy, decellularization cell replacement or inflammatory modulation.

Methods further comprising disconnecting the extracorporeal organ, tissue, or bioengineered graft from the cross circulation circuit and transplanting the extracorporeal organ, tissue, or bioengineered graft into a recipient organism.

Notable methods include those wherein the tissue or bioengineered graft comprises lung, heart-lung, liver, kidney, gut, or limb tissue; wherein the tissue or bioengineered graft comprises lung tissue; wherein the extracorporeal organ is a lung heart-lung, liver, kidney, gut, or limb; wherein the extracorporeal organ is a lung; or wherein the extracorporeal organ is a liver.

The method wherein the extracorporeal organ, tissue, or bioengineered graft exhibits ischaemic injury prior to treatment; such as wherein the ischaemic injury is characterized by consolidation, atelectasis, non-uniform perfusion, airway oedema or abundant cellular content in bronchoalveolar lavage fluid.

The method wherein the extracorporeal organ, tissue, or bioengineered graft exhibits at least one of resolution of airway oedema, recruitment of atelectatic lung, reduction of myeloperoxidase activity, fewer cells in bronchioalveolar lavage fluid, or uniform perfusion of the lung after treatment.

The method wherein the acute injury comprises tissue damage due to exposure to a corrosive or toxic agent, excessive cold, excessive heat, blunt force trauma, laceration or dismemberment.

The method wherein the acute injury is characterized by necrosis, ulceration, inflammation, contusion, hemorrhage, lesions, or ecchymosis.

The method wherein the corrosive agent is an acidic agent.

The method wherein the corrosive agent comprises gastric contents.

The method wherein the acute injury is the result of aspiration of gastric contents.

The method wherein the extracorporeal organ, tissue, or bioengineered graft exhibits at least one of resolution of necrosis, ulceration, inflammation, contusion, hemorrhage, lesions, or ecchymosis after treatment.

The method wherein the organ exhibits a reversible pathologic condition prior to treatment; such as wherein the organ exhibits steatosis, such as in the liver.

The method wherein the organ exhibits reversal of the pathologic condition after treatment, such as reduced triglycerides in cells other than adipocytes; such as in the liver.

The methods can be accomplished by using any of the systems or devices described above.

DETAILED DESCRIPTION OF THE DISCLOSED SUBJECT MATTER

Figure 1A:
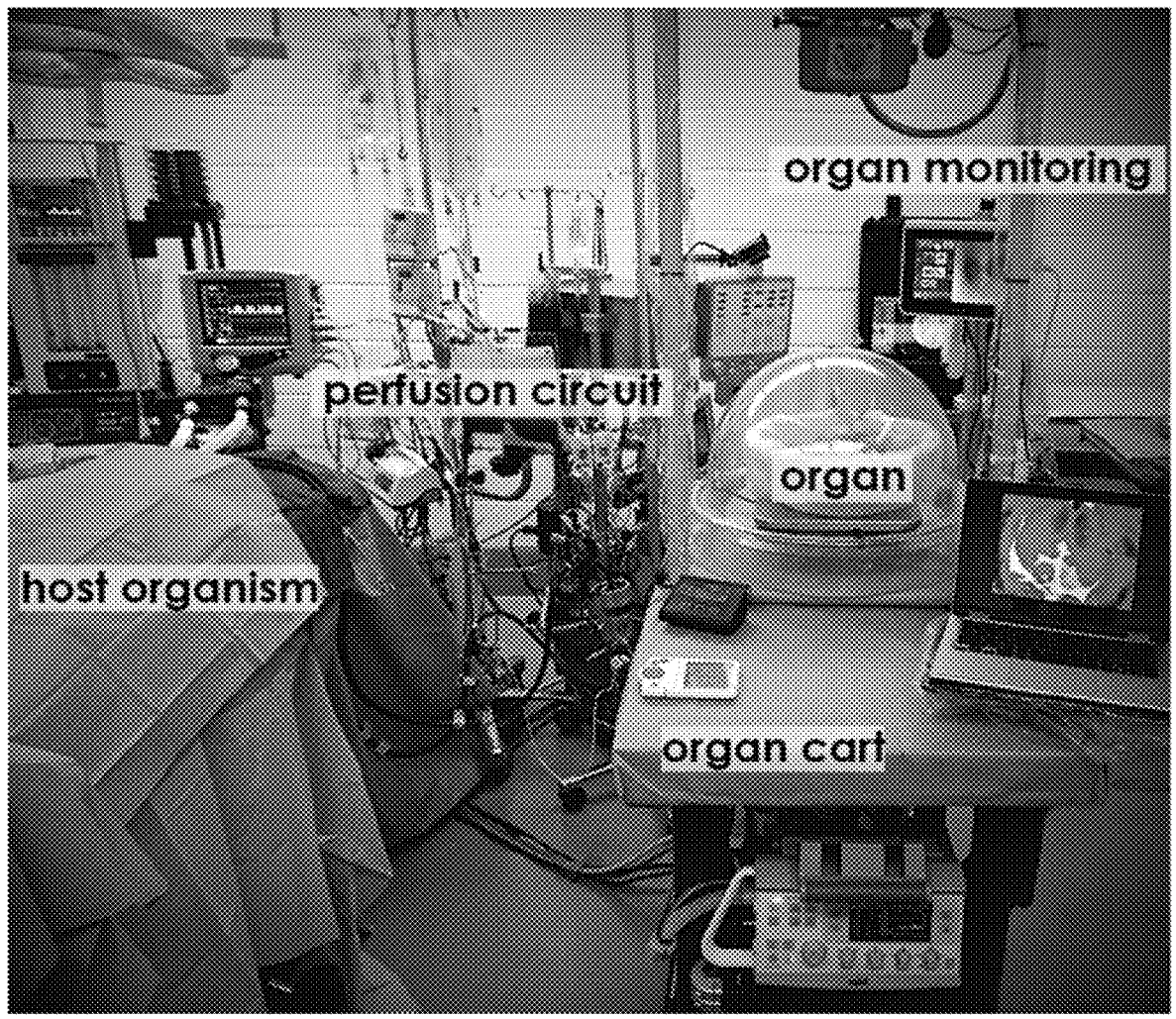
FIGS. 1A and 1B show photographic images of the cross-circulation system for maintaining an extracorporeal organ, tissue, or bioengineered graft.

While methods, systems and devices are described herein by way of examples and embodiments, those skilled in the art recognize that the methods, systems and devices for cross circulation support of extracorporeal organs are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to.

Most donor lungs and many other organs are rejected for transplant after operative assessment during harvest. This invention enables long term preservation (days to weeks) of organs with the maintenance of viability and function with direct donor-host assessment. Such capability is provided for a number of different organs using essentially the same technology. The times are sufficient for various types of intervention (conditioning, oxygenation, cell removal and delivery, gene correction and many others). The invention may enable an increased pool of organs for transplant by allowing for recovery, regeneration, and maintenance of viable and functional donor organs and tissues over times sufficient for therapeutic intervention, including but not limited to: conditioning prior to transplant, gene transfer to correct disease, cell removal/delivery. Additional applications include but are not limited to studies in xenotransplantation and drug therapy.

Provided herein is a mobile platform or system for prolonged (days to weeks) extracorporeal support of an organ, tissue, or bioengineered graft by "cross-circulation" (XC) via connection of a host (e.g., animal, patient, organ transplant recipient). The connection is made directly between the host vasculature and the extracorporeal organ, tissue, or bioengineered graft.

The platform can be used for recovery, regeneration, and maintenance of viable and functional donor organs and tissues over times sufficient for therapeutic intervention, including but not limited to: conditioning prior to transplant, gene transfer to correct disease, cell removal/delivery. Additional research applications include but are not limited to studies in xenotransplantation, theranostics, organ physiology, drug therapy and stem cell therapy.

The system may be used for cross-circulation between the organ recipient and the donor organ. The system may also be applied using a healthy animal (e.g. a normal animal for research uses or an optionally humanized animal for clinical uses) in place of the organ recipient (patient) as the cross-circulation host.

The system provides for the functional recovery of donor lungs injured by ischemia reperfusion (in a large animal model), and may be used to recover lungs more severely damaged by gastric aspiration or other physical or physiologic insults. Applications of the system disclosed herein may provide for the recovery of injured human donor organs specifically using an animal (e.g., pig) genetically modified to have reduced immunologic interaction with human organs or tissues, i.e., a humanized animal 'bioreactor' or human-xenogeneic bioreactor.

This human-xenogeneic bioreactor application takes advantage of the system and procedure described herein with the substitution of the patient with a healthy genetically-modified animal, serving as the xenogeneic bioreactor. The benefits conferred to the extracorporeal organ by cross-circulation with a porcine organ-porcine recipient system or human organ-human recipient system may be similar for a human organ-xenogeneic recipient system. This human-xenogeneic bioreactor support system would also be applicable to other transplantable organs, grafts, and bioengineered tissues.

The human-xenogeneic bioreactor may provide significantly expanded ability to recover a greater number of injured donor organs. Furthermore, additional uses of a human-xenogeneic bioreactor may include use in gene therapy, immunomodulation, organ physiology, xenotransplantation, pharmacologic agents, and other organ modification and repair strategies.

The cross-circulation platform represents a substantial opportunity for the recovery, regeneration, and maintenance of sub-optimal donor organs (lung, liver, kidney, pancreas, injured limb, etc.) for transplantation.

In one aspect, systems, methods and devices for cross-circulation support of extracorporeal organs including heart, lung, heart/lung, liver, pancreas, kidney, small intestine, bioengineered grafts and xenogenic organ grafts are provided. Envisioned uses of cross-circulation between an organ recipient and extracorporeal organ include rescue of donor organs unacceptable for transplantation, salvage of traumatized limbs, or support of bioengineered or xenogeneic organ grafts. Both conventional EVLP and cross-circulation allow for administration of energy substrates, maintenance of barrier integrity, organ function assessment and oedema clearance. Cross circulation infusion offers extended extracorporeal support (greater than 24 hours and a greater range of therapies compared to conventional isolated ex vivo lung perfusion (EVLP), providing an extended period of extracorporeal organ viability for organs prior to transplant. Benefits that cross-circulation of a recipient's blood confers to the extracorporeal organ include increased recovery time, the ability to provide energy substrates, circulating repair factors, metabolic clearance, and allow for extended immunological and graft performance assessment.

Cross circulation perfusion also enables a variety of therapeutic interventions, including medication, drug nanoparticles, gene therapy, stem cell therapy, decellularization cell replacement and inflammatory modulation, in donor organs unacceptable for transplantation, which could significantly expand donor organ pools by allowing recovery of organs and tissues that were previously unacceptable for transplantation. For example, this is the first technology that allows the maintenance of human lungs outside the body without oedema for days to weeks, which provides a viable platform for genetic and phenotypic modification of the organ to improve compatibility matching. Delivery of bioactive or therapeutic agents to the extracorporeal lung can be by intratracheal delivery of CFSE, microbeads, and stem cells (including mesenchymal stem cells) for example. Native cells can be harvested, de-epithelilialized and recellularized for decellularization cell replacement therapy. Transpleural imaging can be used to examine the extracorporeal lung and/or guide delivery of agents to specific portions of the lung.

The present embodiments demonstrated successful maintenance of organ function, tissue architecture, and cellular/microscopic integrity of an extracorporeal organ (lung) for at least 36 hours. Such results were enabled by the system (i.e., setup and circuit) of cross-circulation between a host and an extracorporeal organ described herein. This represents unprecedented results with respect to quality and duration of organ preservation and performance after 36 hours outside the body. After 36 hours, all lungs were shown to meet transplant criteria.

To overcome the limitations of EVLP, we developed a 'cross-circulation' platform using a clinically relevant swine model. Early attempts at cross-circulation between two humans utilized a healthy individual to support and augment the organ function of a patient suffering from a critical but potentially reversible illness given sufficient time for recovery (for example, hepatic insufficiency, uraemia, eclampsia).

The various embodiments of the invention can be understood by reference to the Figures.

Figure 1B:
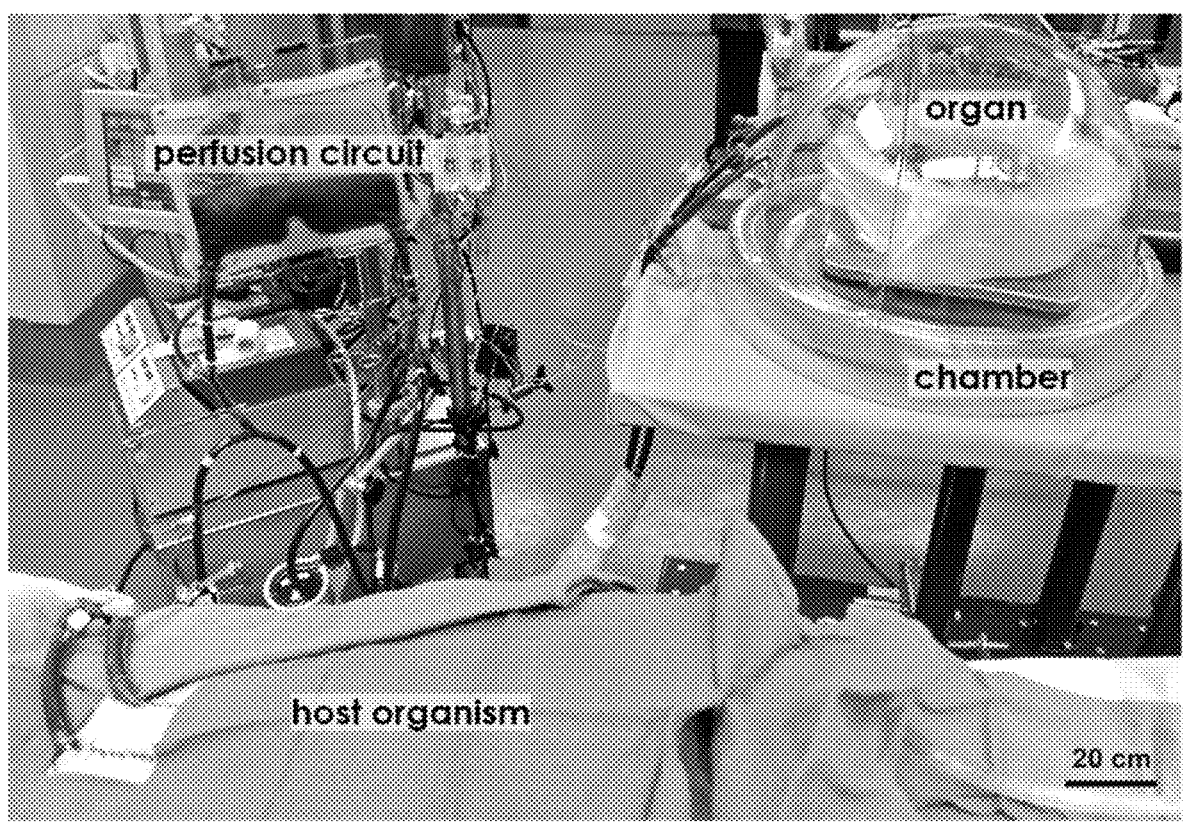

FIGS. 1A and 1B show photographic images of the cross-circulation system. FIG. 1A shows an operating room setup of the cross-circulation system. The host organism, under surgical drapes, is connected to an extracorporeal organ in the organ chamber via the perfusion circuit. The chamber is placed on an organ cart that can be used to raise and lower the chamber to modulate the blood pressure difference between arterial and venous pressures. Organ monitoring stations are shown in the background. FIG. 1B shows a closer view of the cross-circulation system, comprising a chamber to contain and support the extracorporeal organ shown in the chamber and a perfusion circuit to connect the organ with a host organism (e.g., organ transplant recipient), wherein the circuit comprises auto-regulation of blood flow based on the trans-organ blood pressure difference between arterial and venous pressures.

The cross-circulation circuit comprises fluid conduits such as tubing and/or cannulae providing fluid connectivity from the vascular system of a host or recipient to the extracorporeal organ vasculature and from the extracorporeal organ back to the host or recipient. The conduits are configured so that fluid, such as whole blood and/or plasma, can form a continuous loop or circuit to support the extracorporeal organ by supplying fluid flow containing oxygen and nutrients to the organ from the host and returning waste and/or metabolites from the extracorporeal organ to the host for clearance.

Figure 11:
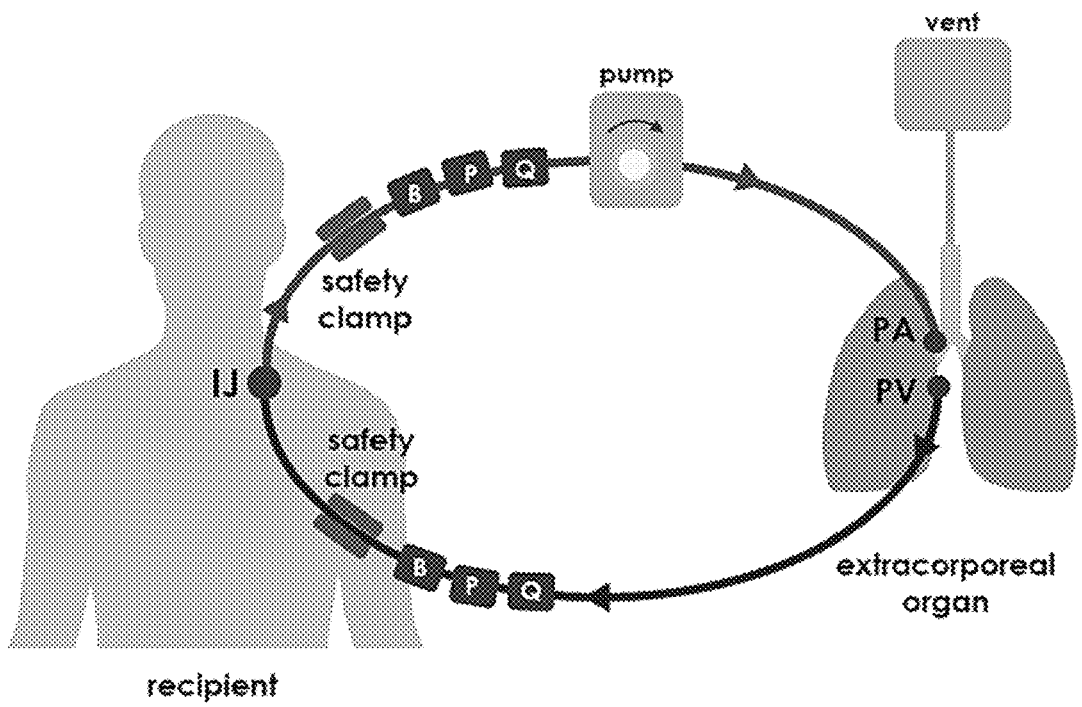
FIG. 11 shows a schematic of a cross-circulation circuit for whole blood comprising patient safety clamps.

FIG. 11 shows a cross-circulation circuit diagram with integrated circuit elements for circulating whole blood through the perfusion circuit, with an additional feature of a safety clamp for halting circulation in the circuit described in more detail below. The elements include: A, airflow probe; B, blood sample port; H, warm water jacket; IJ, internal jugular vein; P, pressure sensor; PA, pulmonary artery; PV, pulmonary vein; Q, flow probe; T, temperature probe.

Figure 2:
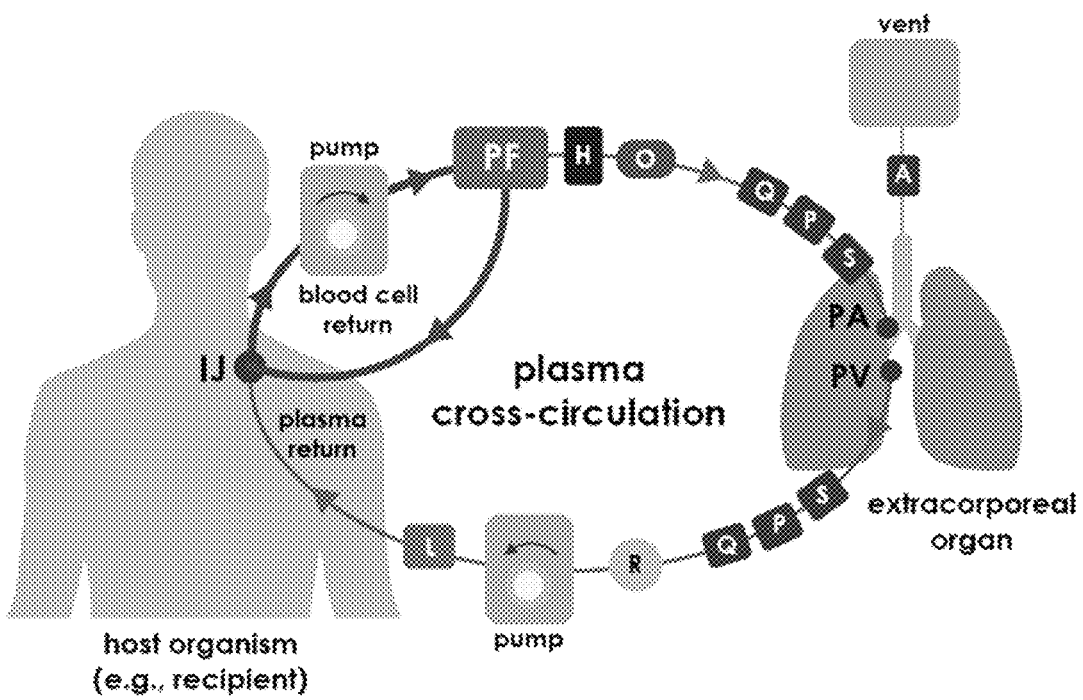
FIG. 2 shows a schematic of a system for cross-circulation of plasma (versus whole blood) to maintain an extracorporeal organ, tissue, or bioengineered graft.

FIG. 2 shows a schematic of a system for cross-circulation of plasma (versus whole blood) to maintain an extracorporeal organ, tissue, or bioengineered graft. The system is similar to the whole blood system but also comprises an extracorporeal circuit containing a filter (PF) that permits return of blood cells directly to the recipient and perfusion of plasma through the extracorporeal organ. A leukocyte reduction filter (L) is located in the circuit segment between the organ and the recipient to prevent any immunologic cells that may exit the extracorporeal organ from entering the vasculature of the host organism.

Figure 3A:
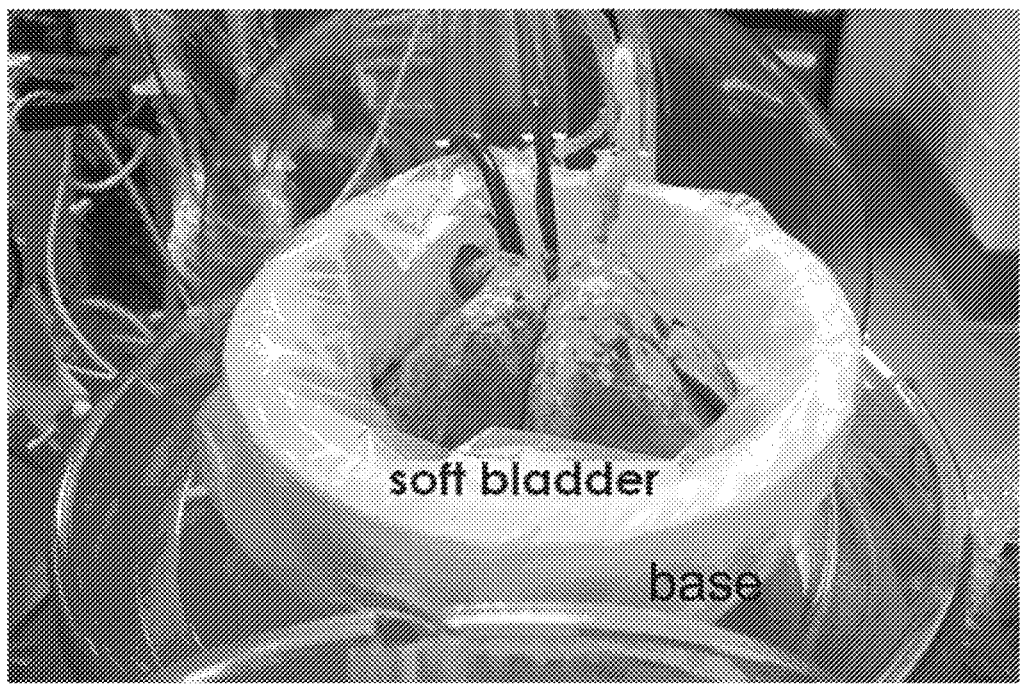
FIGS. 3A to 3E show photographic images of the organ chamber basin.
Figure 3B:
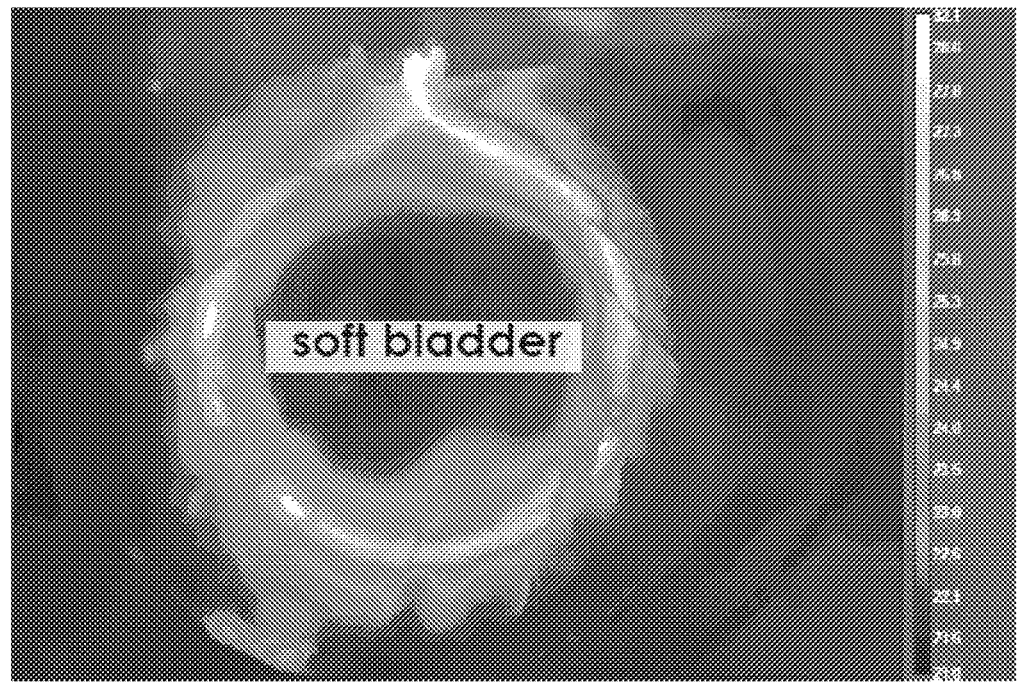
Figure 3C:
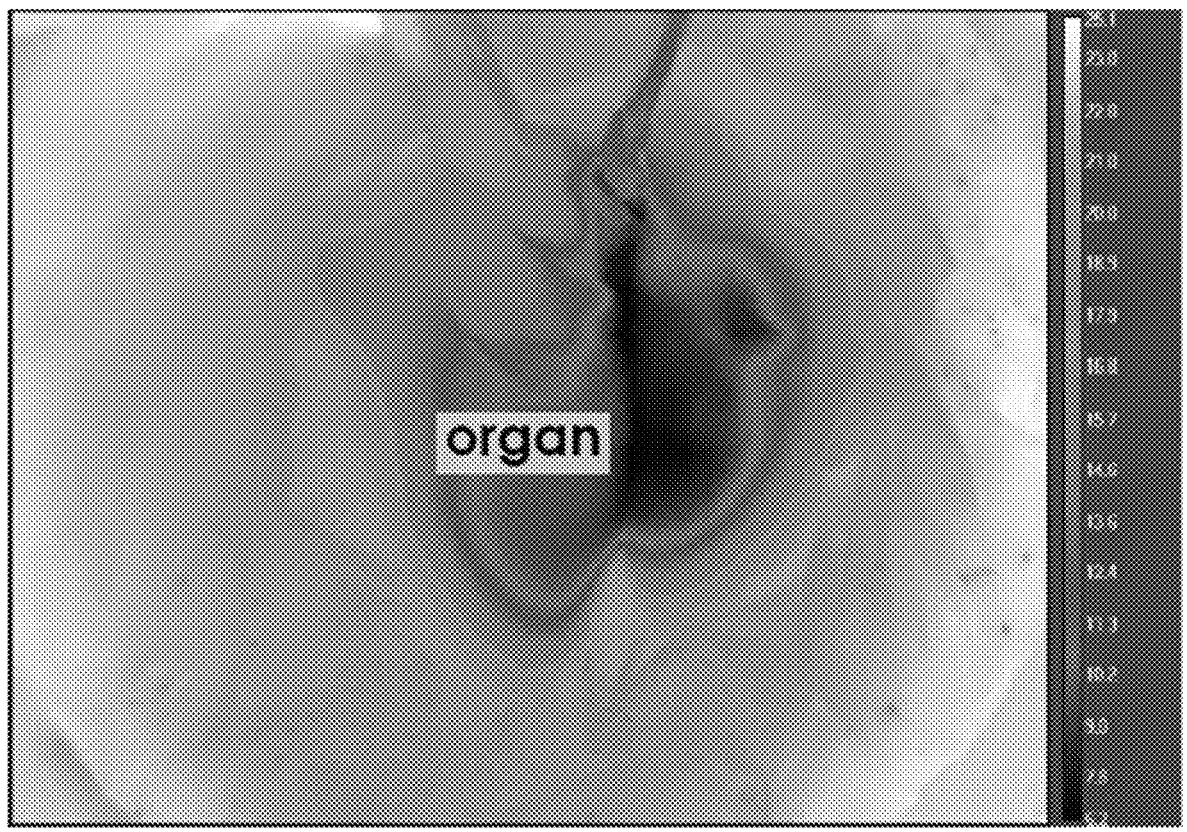
Figure 3D:
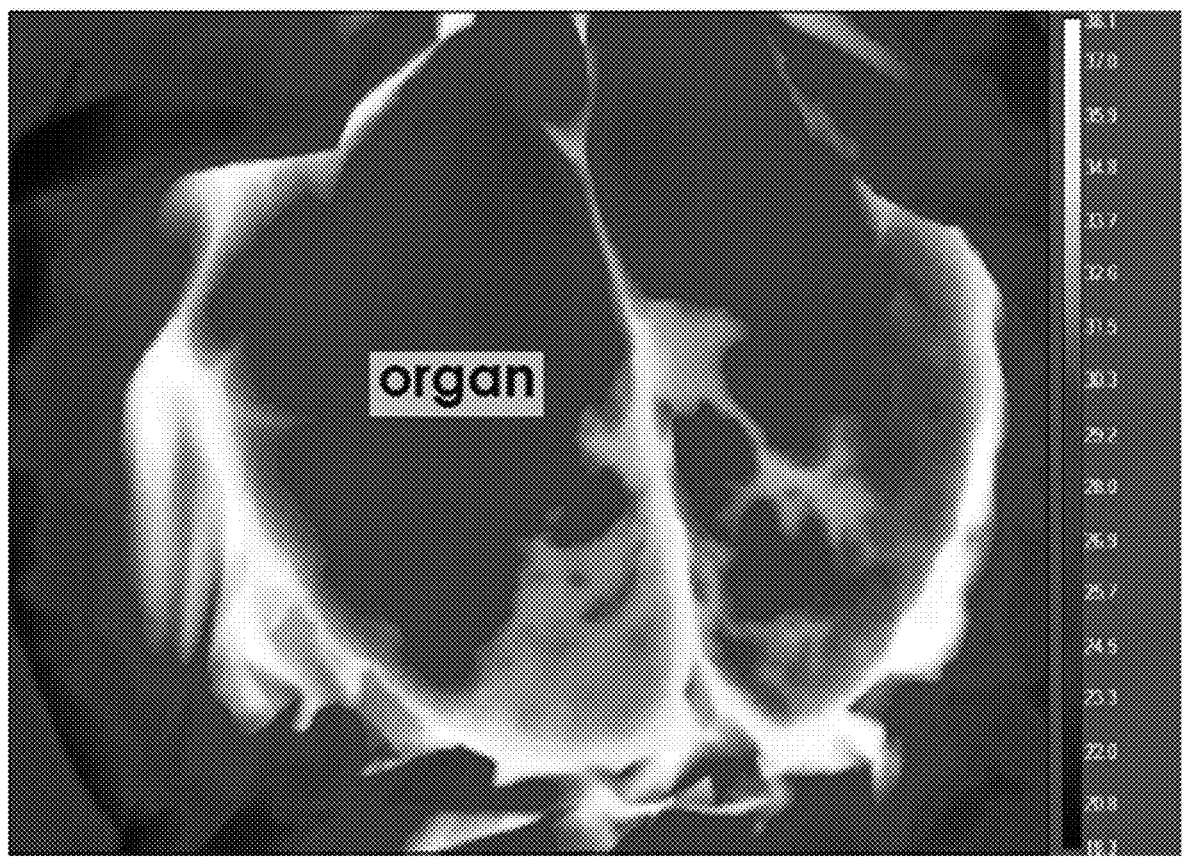
Figure 3E:
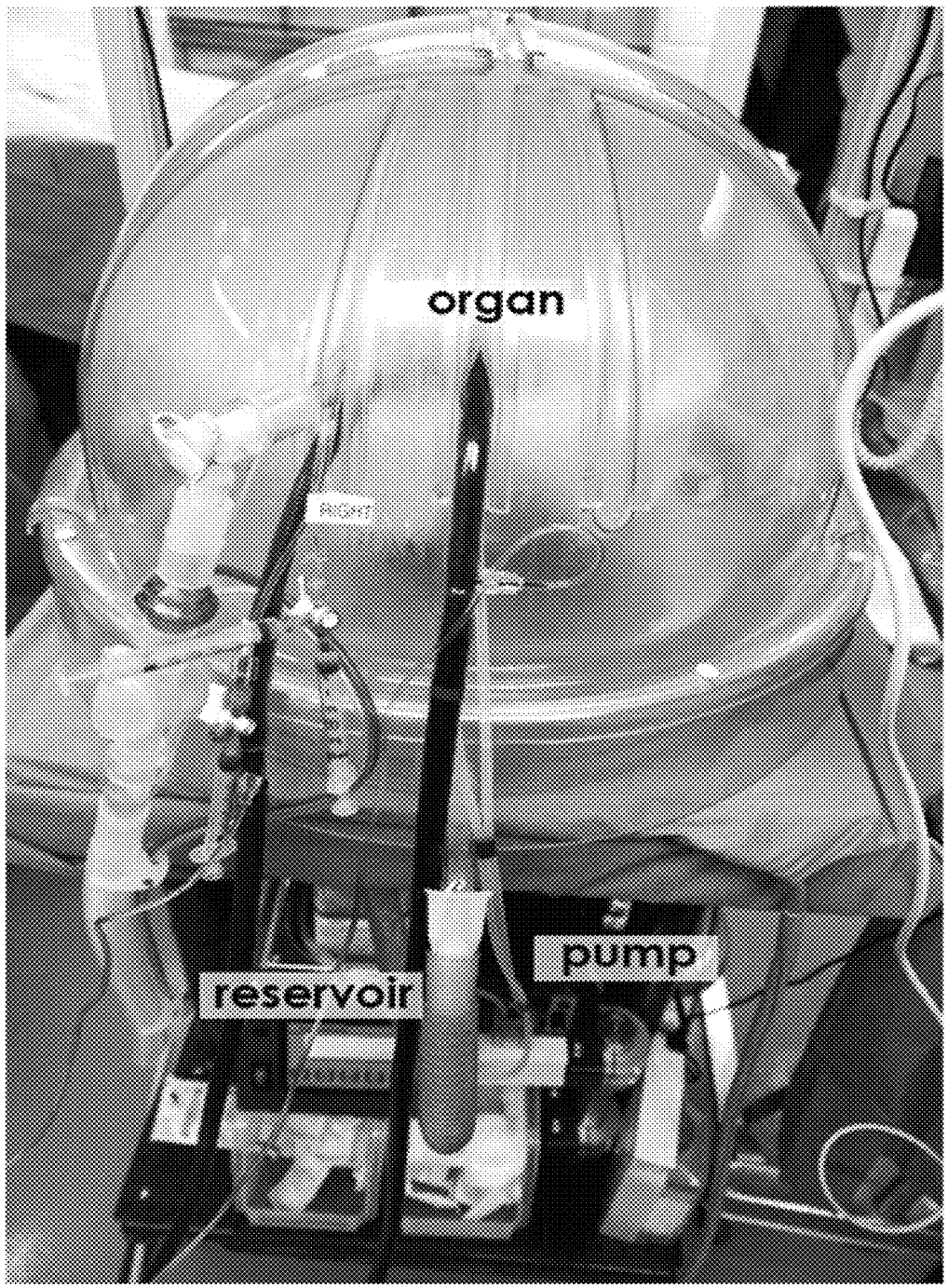

FIGS. 3A to 3E show the organ chamber basin. In FIG. 3A, the chamber comprises a soft bladder onto which the organ is placed, with temperature-controlled bladder interior maintained with recirculating temperature-controlled water in a range from 4° C. to 40° C. for externally and uniformly either warming the organ at the initiation of cross-circulation or cooling the organ at the conclusion of cross-circulation. FIGS. 3B-3D show thermal imaging of the organ in the chamber. 3B shows the warm water circulating loop as a bright ring surrounding darker (colder) organ, such as when the organ is placed in the chamber after cold storage. 3C shows the organ being warmed at the beginning of cross-circulation and 3D shows the organ being cooled at the conclusion of cross-circulation. FIG. 3E shows that warm or cool water is continuously recirculated from a temperature-controlled reservoir by a pump to achieve a constant soft bladder temperature in a range from 4° C. to 40° C., such as from 4° C. to 37° C. or from 30° C. to 40° C. or from 35° C. to 40° C.

Figure 4A:
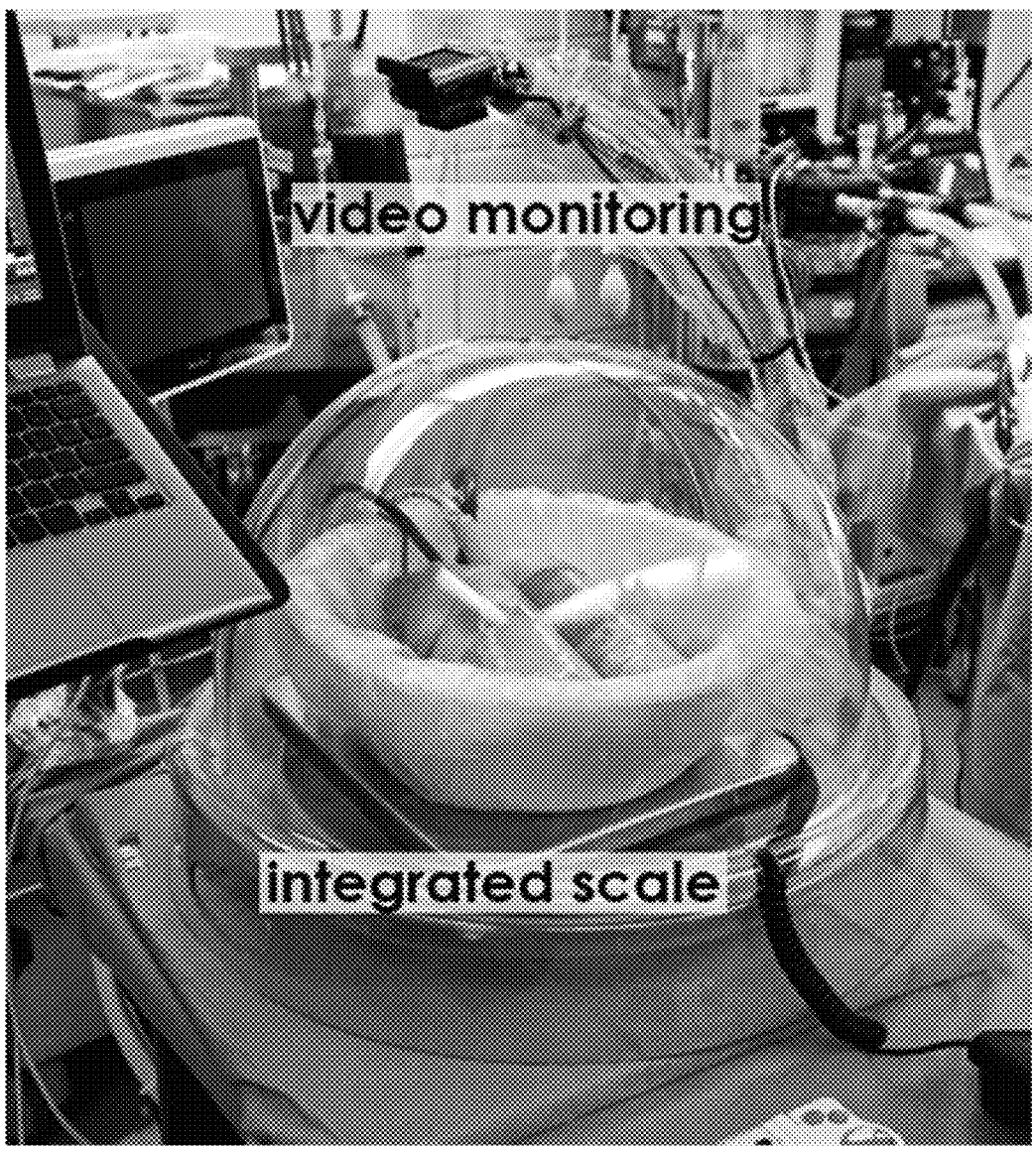
FIGS. 4A to 4C show additional photographic images of the organ chamber basin.
Figure 4B:
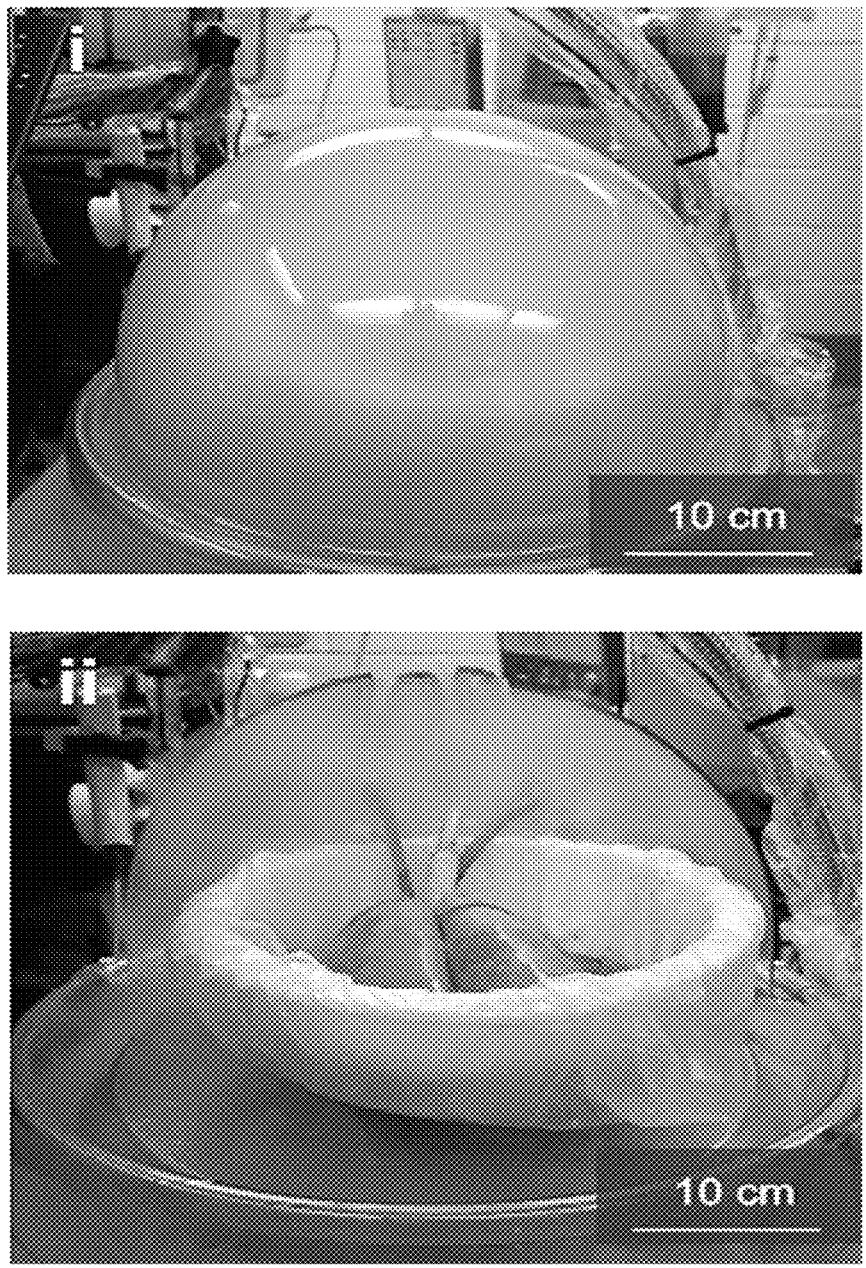
Figure 4C:
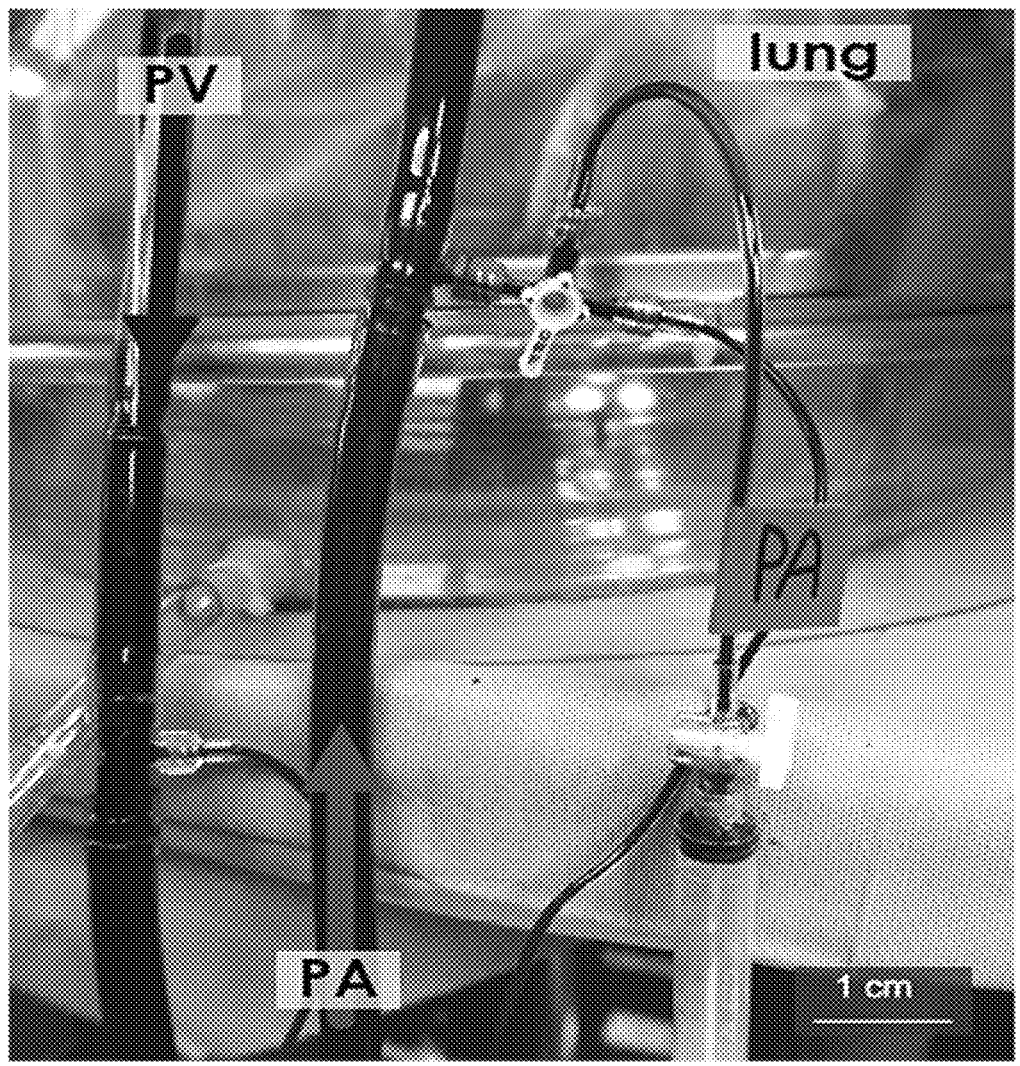

FIG. 4A shows the extracorporeal organ, tissue, or bioengineered graft chamber. The chamber contains an integrated scale for monitoring and recording organ weight and real-time macroscopic video recording of the organ with remote monitoring capabilities. FIG. 4B shows images of the chamber during operation of a time- and temperature-controlled humidifier and misting spray onto the organ and into the organ chamber to maintain a humid environment within the chamber. FIG. 4C shows access ports for sterile sampling of blood (from PA: pulmonary artery; PV: pulmonary vein) and tissue.

Figure 5A:
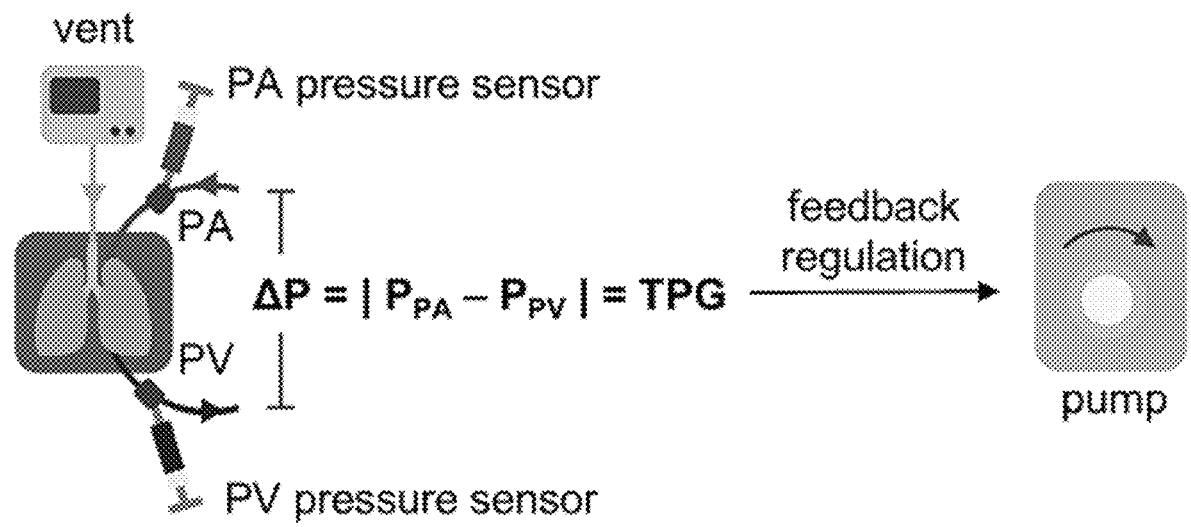
FIGS. 5A and B show aspects of the control of cross-circulation perfusion of an extracorporeal organ, tissue, or bioengineered graft.
Figure 5B:
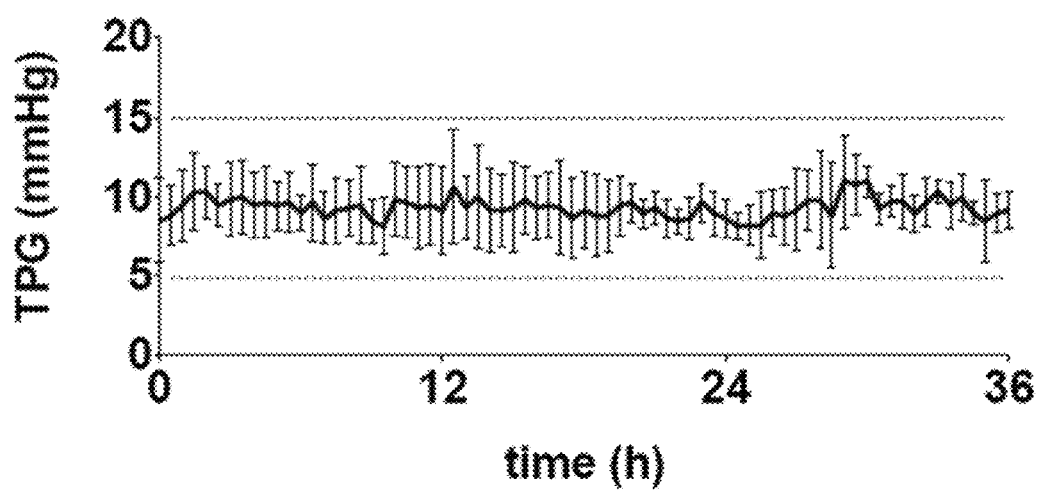

FIGS. 5A and B show aspects of the control of cross-circulation perfusion of an extracorporeal organ, tissue, or bioengineered graft. FIG. 5A shows a schematic of the organ with pressure sensors on arterial and venous sides of the organ enabling pressure-controlled, adjustable blood flow with organ-specific trans-organ pressure feedback regulation to a circulating pump. FIG. 5B shows a representative graph of the Transpulmonary Pressure Gradient (TPG) within an organ-specific range over 36 hours of cross-circulation to maintain an optimal trans-organ vascular pressure gradient.

Figure 6A:
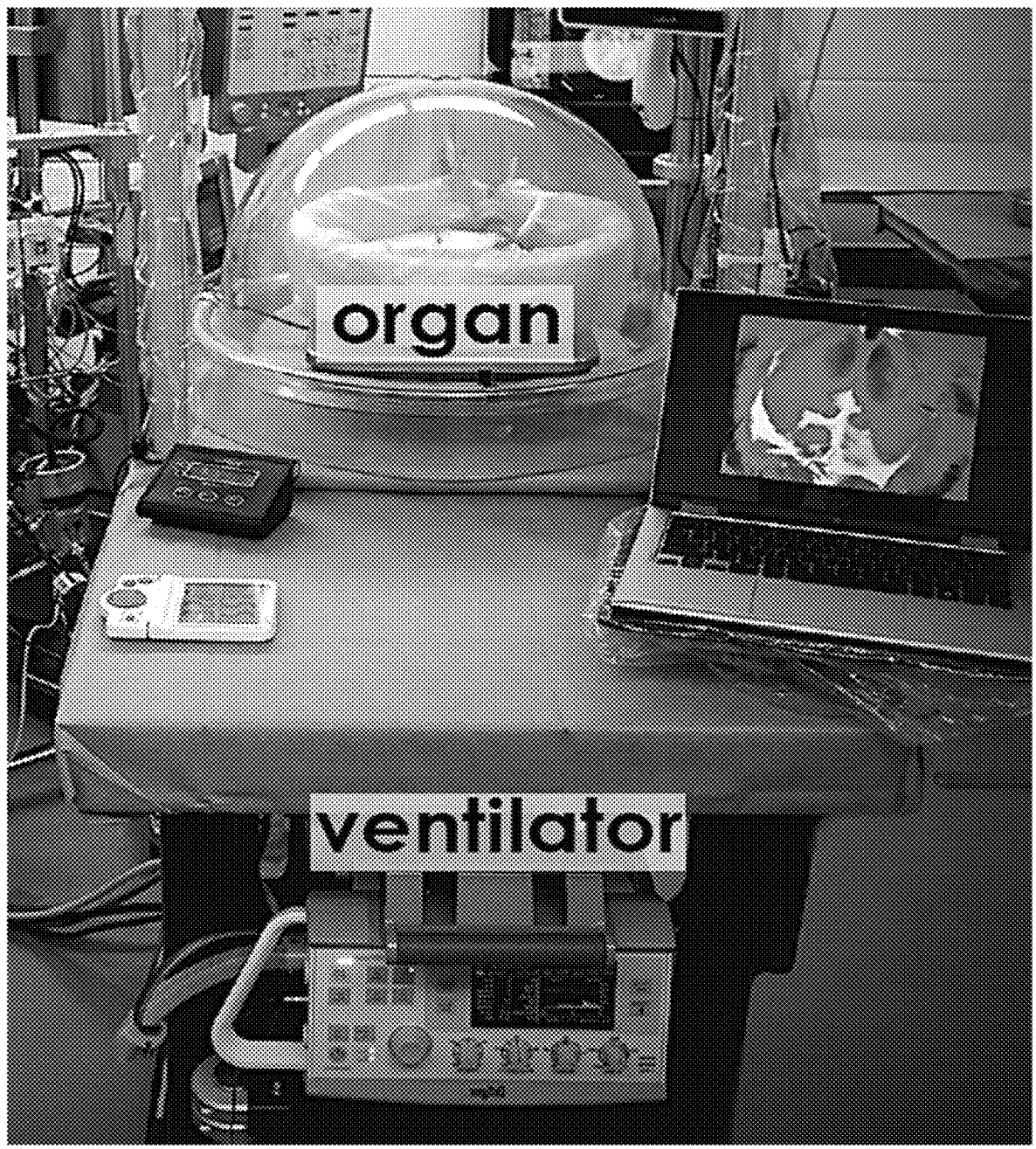
FIGS. 6A to 6C show aspects of a chamber cart or stand for maintaining an extracorporeal organ, tissue, or bioengineered graft.
Figure 6B:
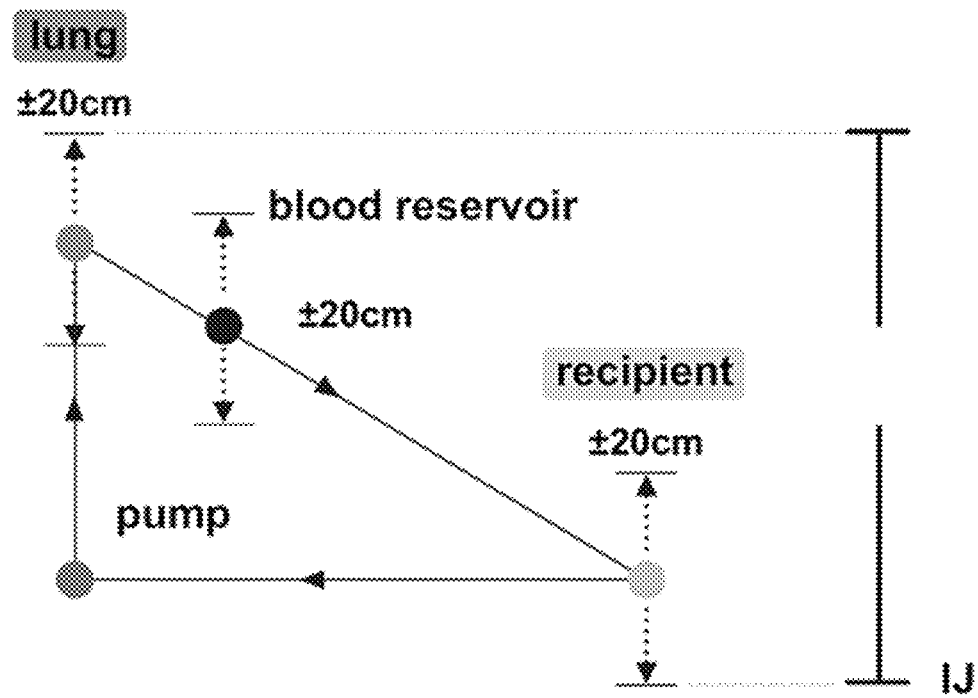
Figure 6C:
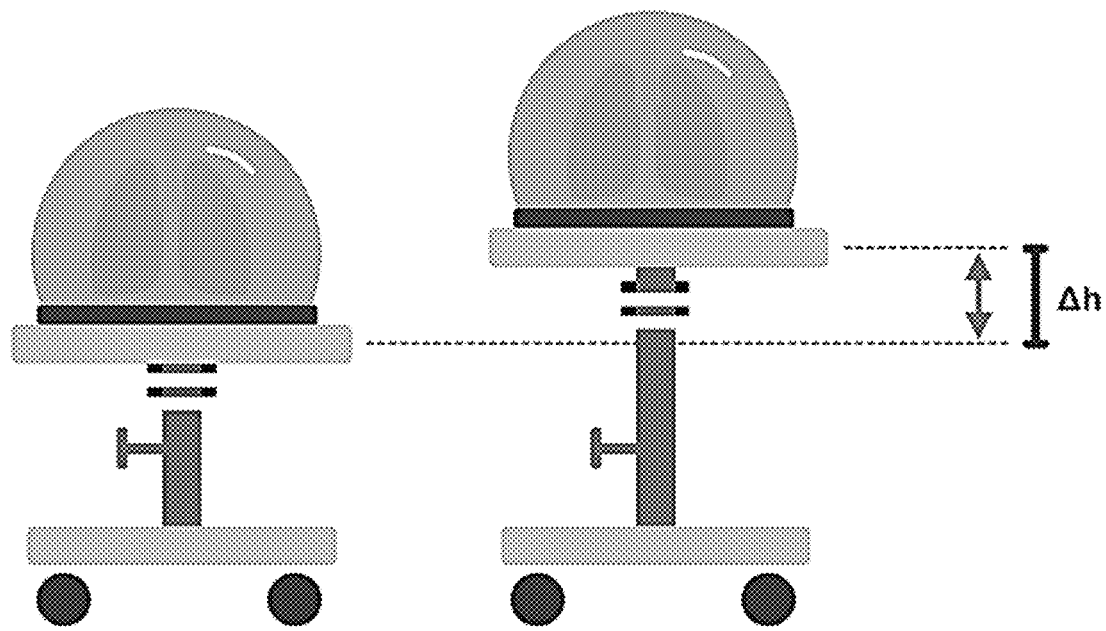

FIG. 6A shows a photograph of an example organ cart or stand equipped with an organ-specific accessory, i.e. a ventilator, for the ventilation and support of extracorporeal lungs on cross-circulation. FIG. 6B shows the use of height differences to modulate extracorporeal bloodflow (triangle) by circuit hydrostatic pressure differences. FIG. 6C shows a schematic of automatic height adjustability of organ cart based on feedback from extracorporeal in-flow and out-flow line blood pressures.

Figure 7A:
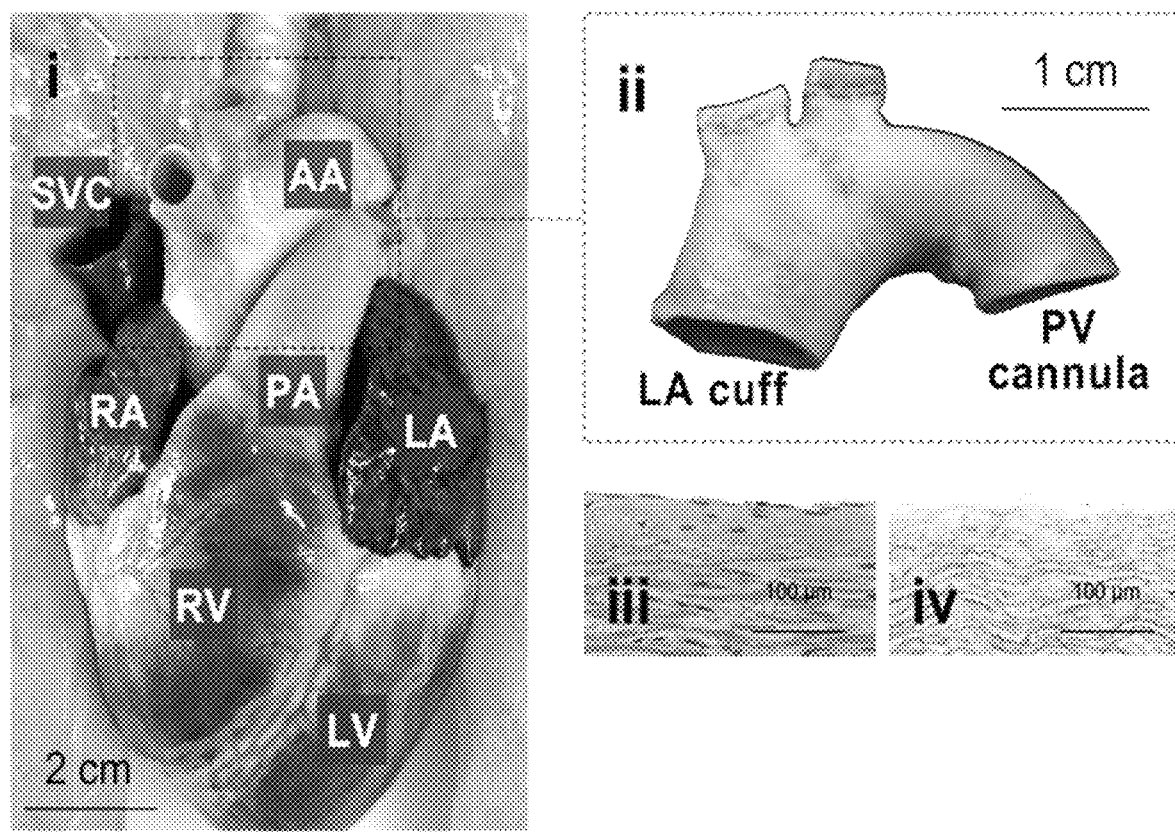
FIGS. 7A to 7E show aspects of the management of pulmonary venous drainage and utilization of donor vessel as a biologic cuff device.
Figure 7B:
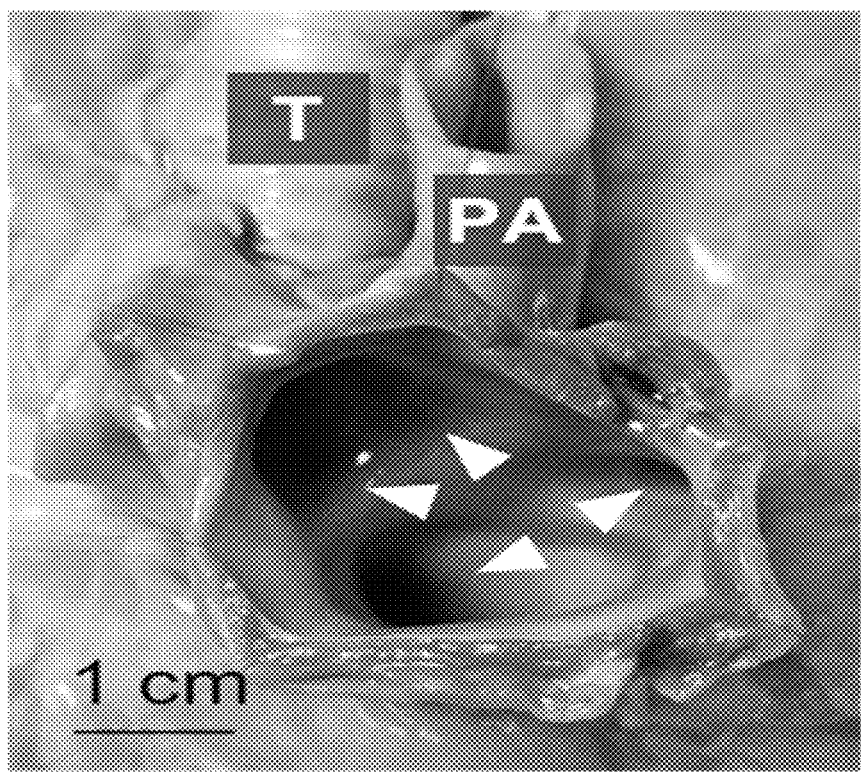
Figure 7C:
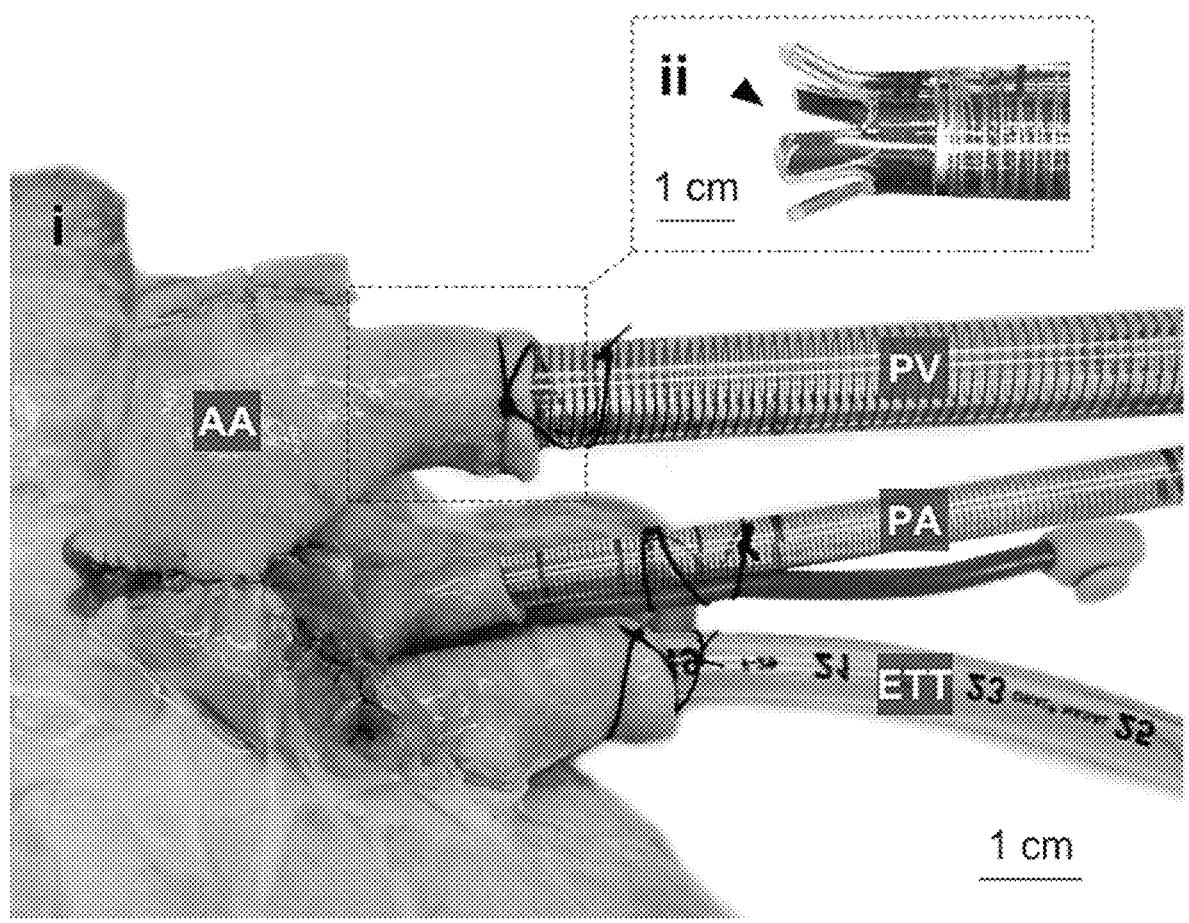
Figure 7D:
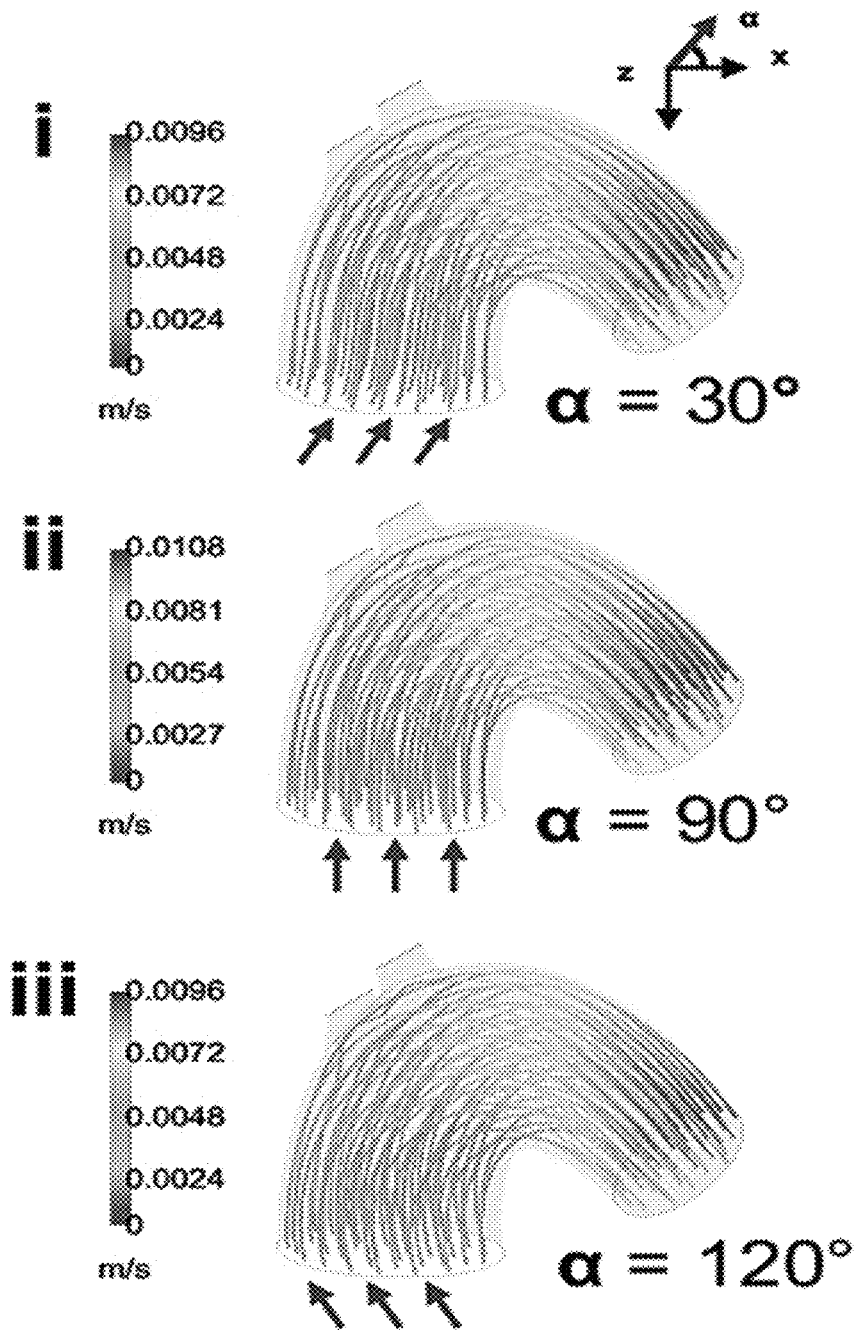
Figure 7E:
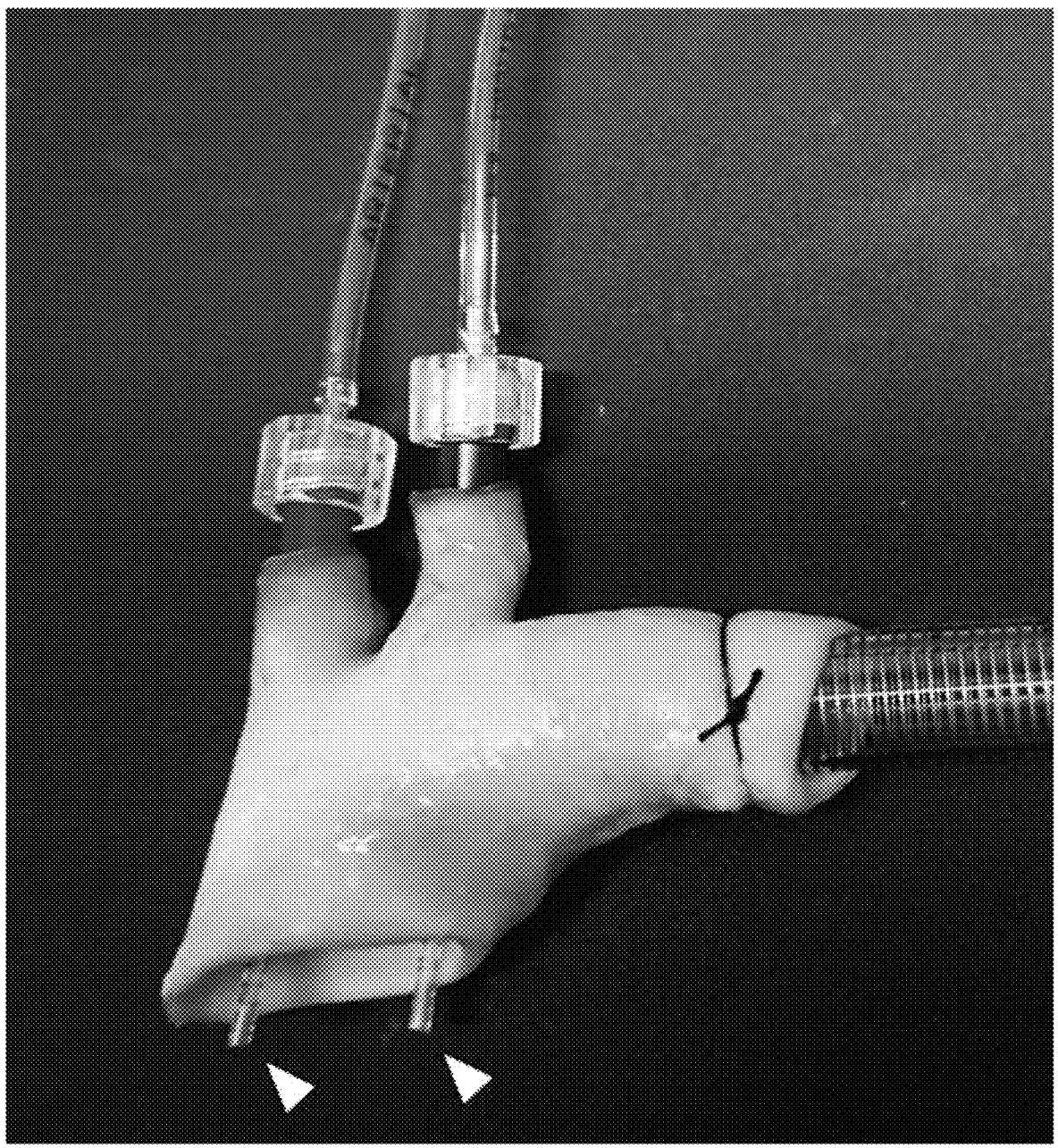

Management of pulmonary venous drainage is achieved using portions of a donor blood vessel as a biologic cuff device. FIG. 7A shows photographs indicating characterization of the biologic cuff device: (i) shows the aortic arch (AA) in situ in a donor heart. SVC: superior vena cava, RA: right atrium, RV: right ventricle, PA: pulmonary artery, LA: left atrium, LV: left ventricle. (ii) shows the AA dissected, with brachiocephalic and left subclavian branches stapled and trimmed for anastomosis to left atrial cuff. (iii) hematoxylin and esosin (H&E) staining of AA showing the endothelialized lining with elastic wall structure of the biologic cuff device. (iv) Silver stain of AA showing reticular fibers supporting the biologic cuff wall. FIG. 7B shows the left atrial (LA) cuff after removal of the heart, revealing the pulmonary veins (arrows). T: trachea. FIG. 7C shows how the biologic cuff device is used to connect organ and cannula. ETT: endotracheal tube. shows of blood demonstrating laminar flow. FIG. 7D shows a three-dimensional computational model simulating blood flow entering the bio-bridge at varying angles. Blood flow streamlines were obtained by computational fluid dynamic simulations at $\alpha=30°$, $90°$ and $120°$. The computational flow dynamics demonstrate laminar flow in the in the biologic cuff device. FIG. 7E shows the biologic cuff device with pressure and flow sensors placed in the head vessels. Tips of sensors (indicated by arrows) reach the 'pseudoatrium' formed by the biologic cuff device.

Figure 8A:
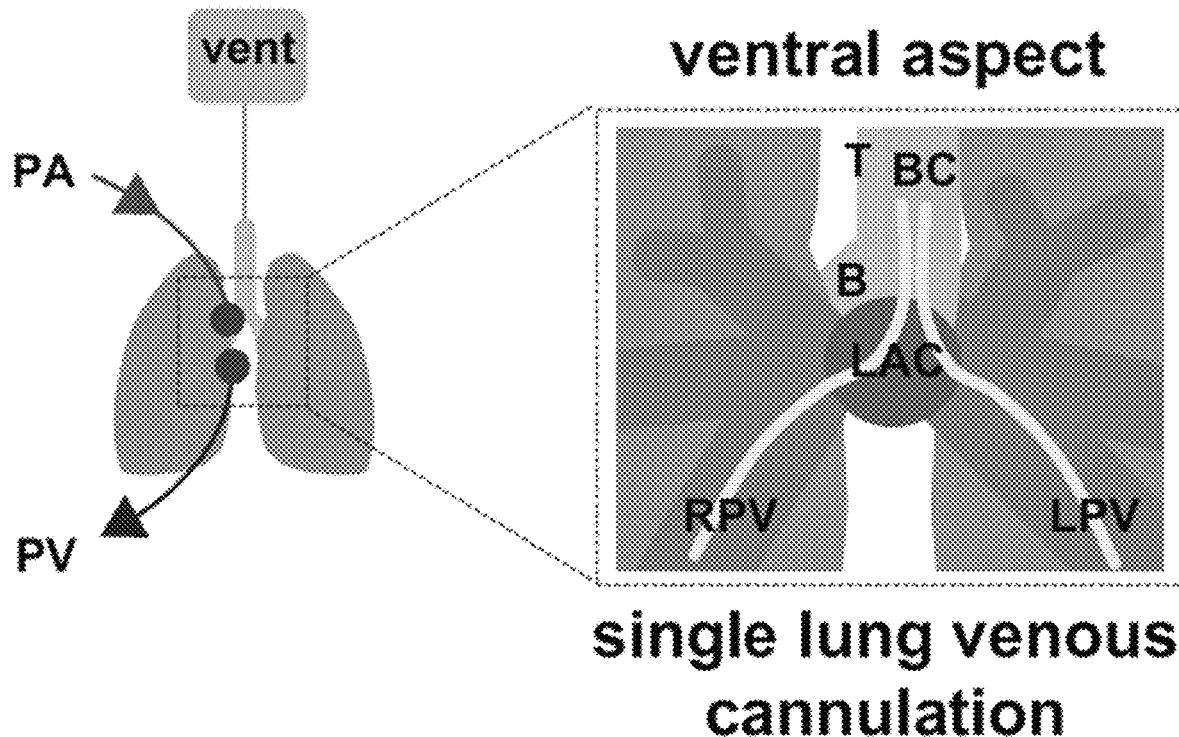
FIGS. 8A to 8H show aspects of the use of a biologic cuff device for single lung venous cannulation.
Figure 8B:
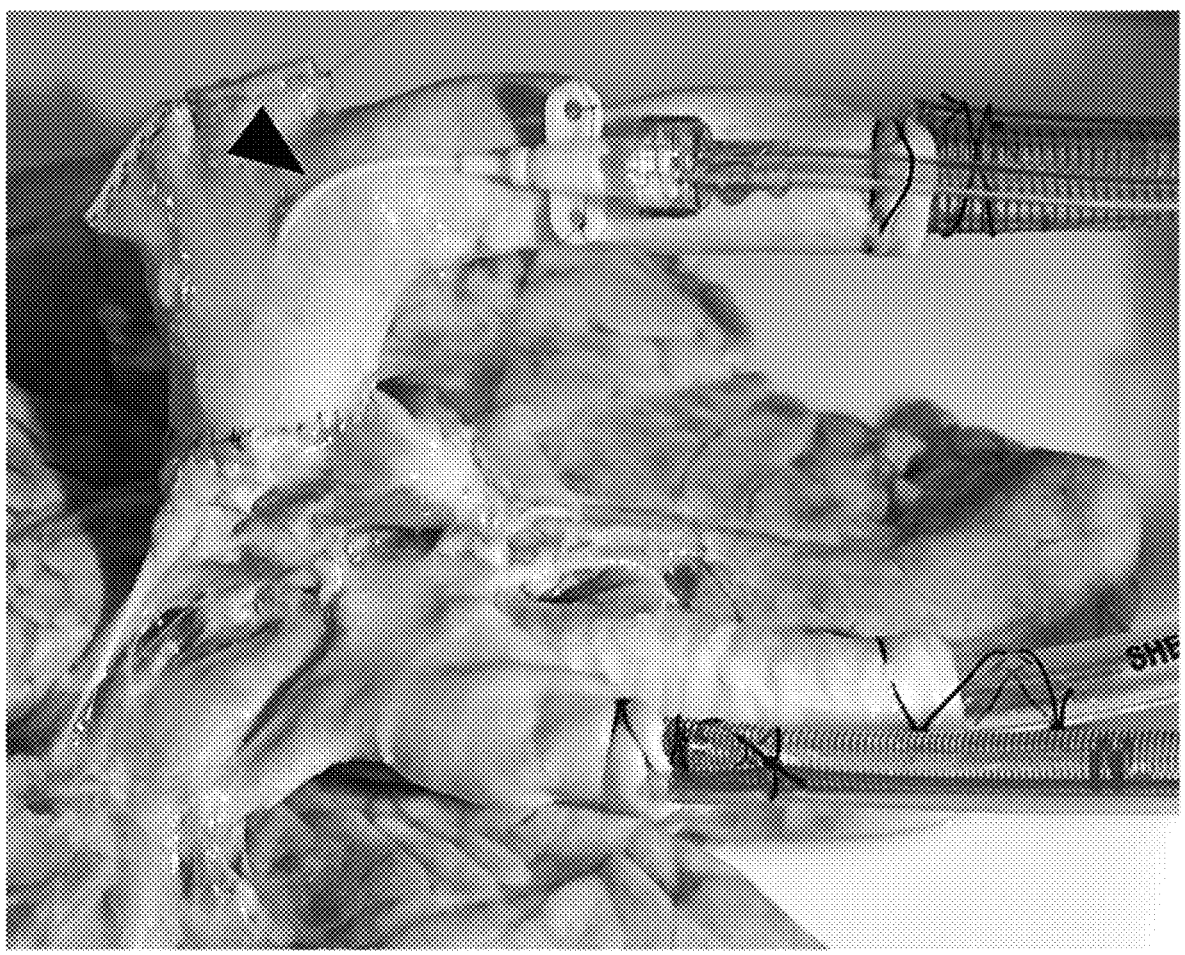
Figure 8C:
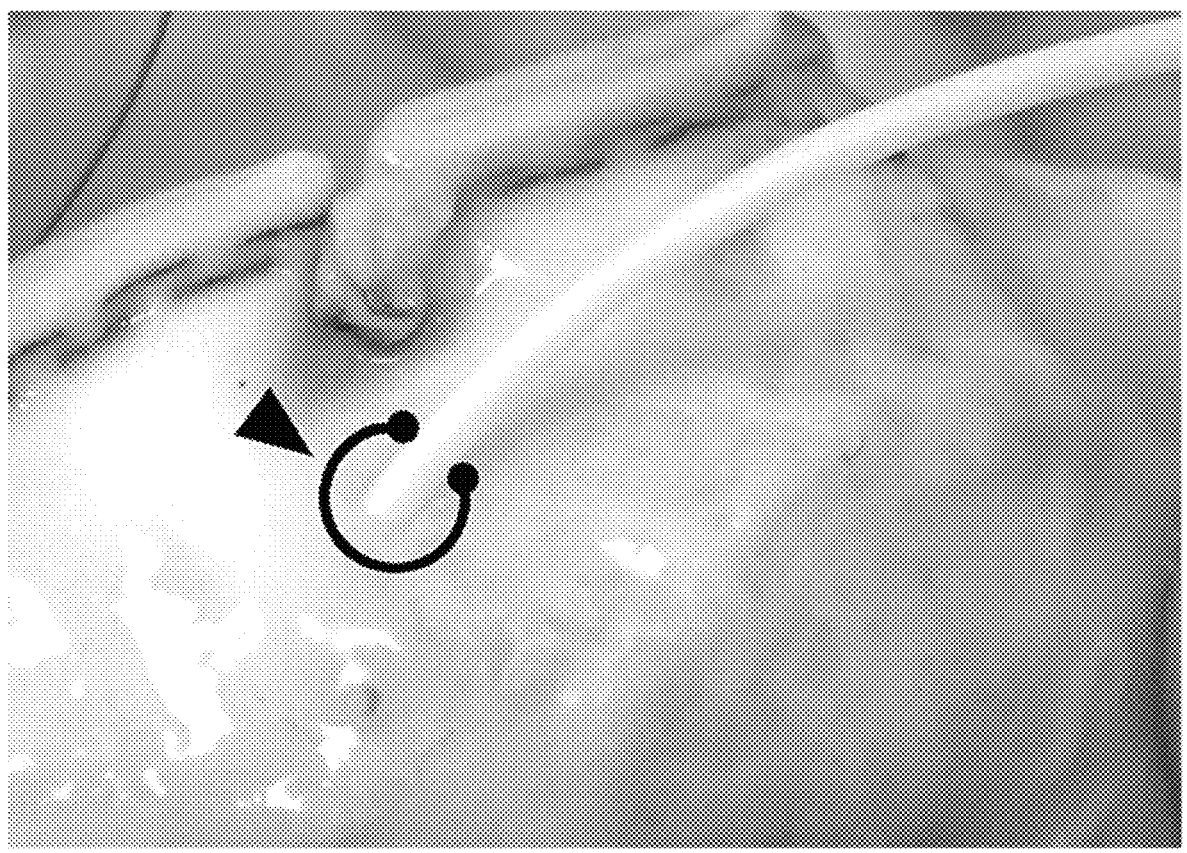
Figure 8D:
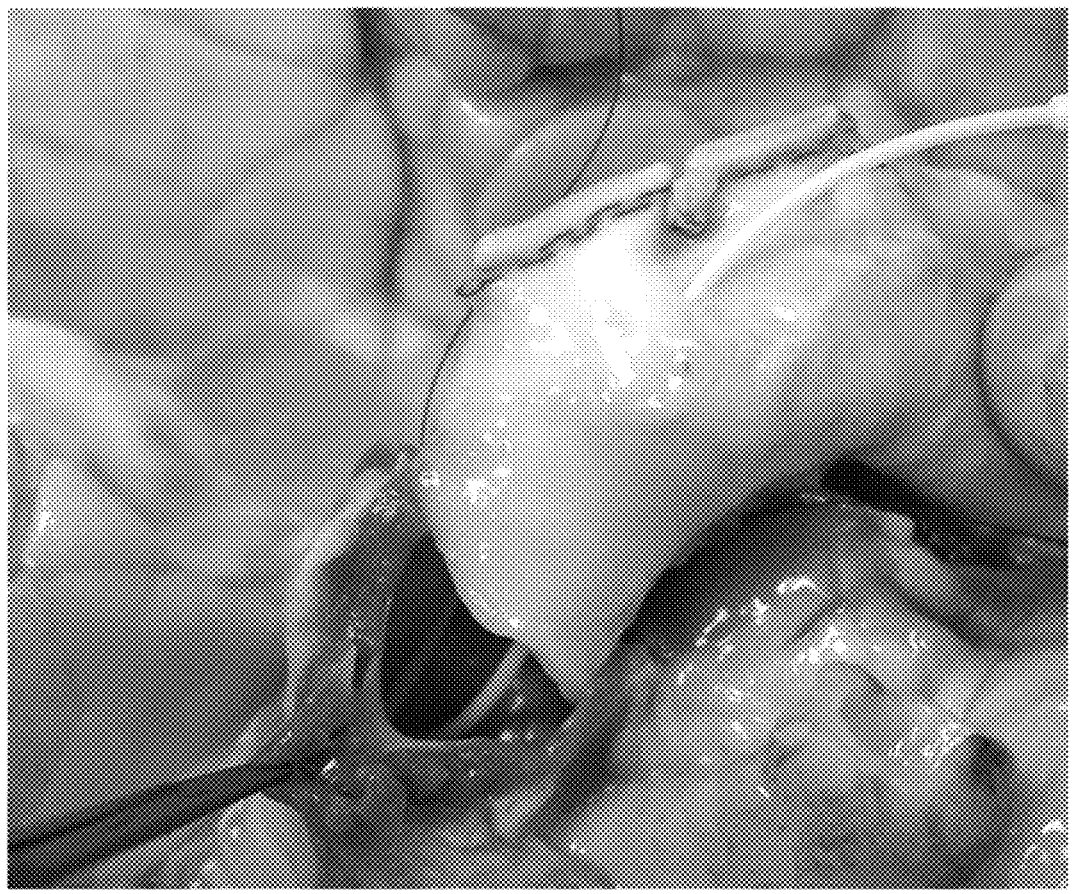
Figure 8E:
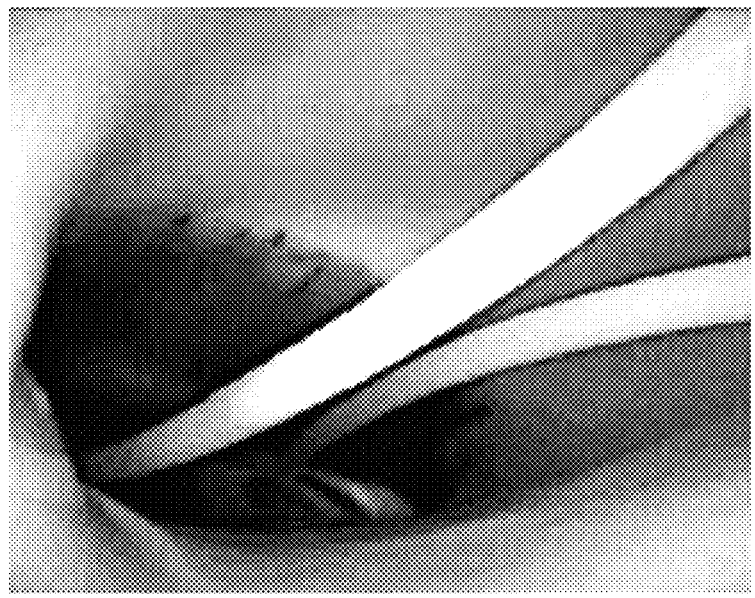
Figure 8F:
Figure 8G:
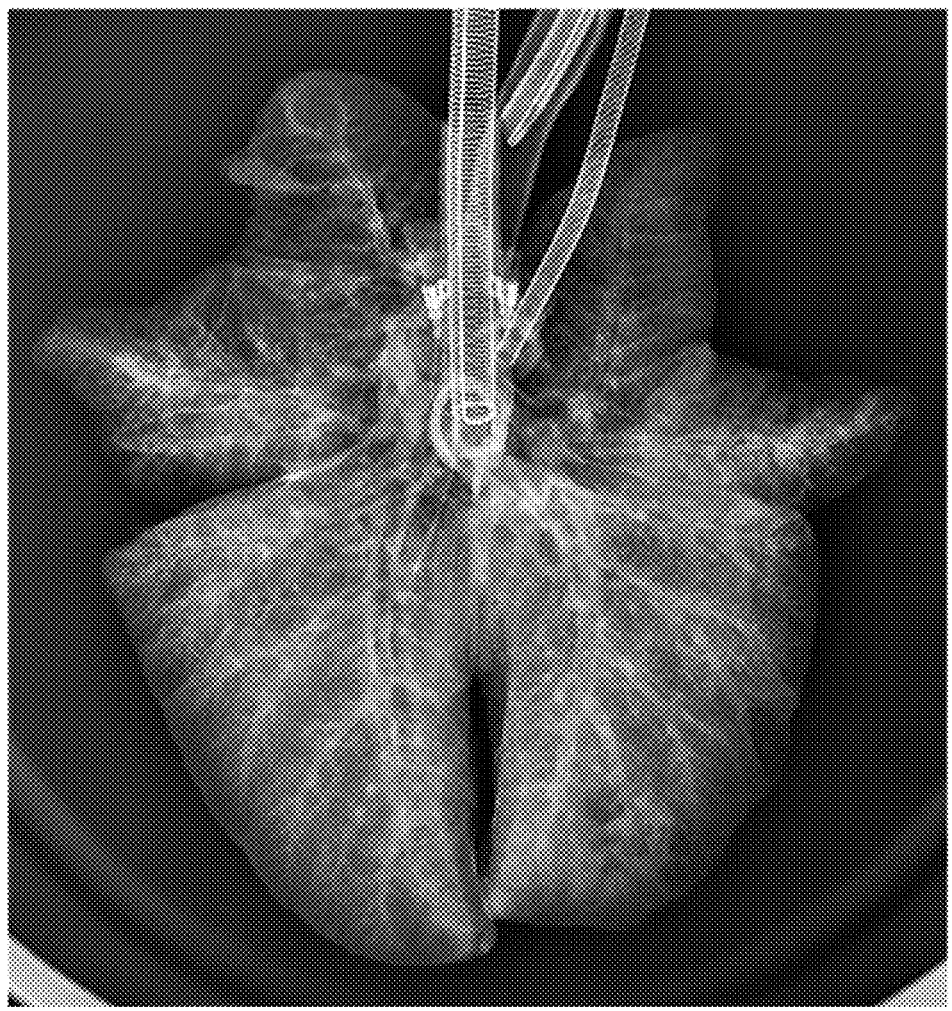
Figure 8H:
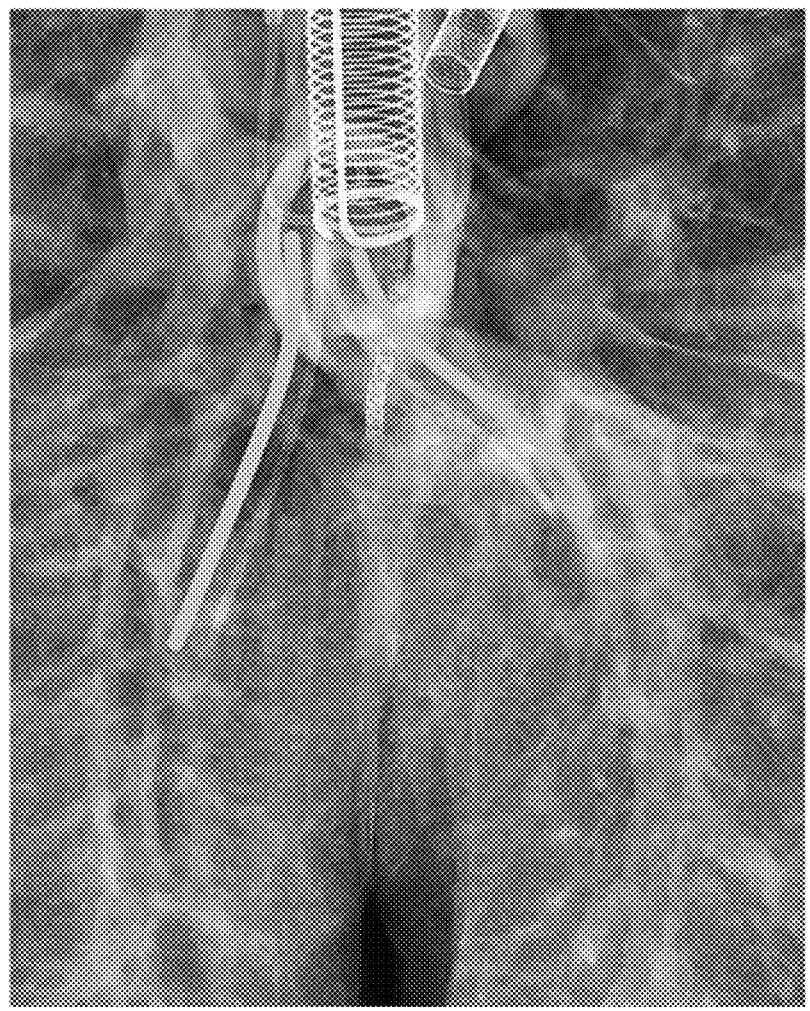

FIGS. 8A to 8H demonstrate the use of a biologic cuff device for single lung venous cannulation. FIG. 8A shows a schematic of single lung venous cannulation with component labels. FIG. 8B shows the biologic cuff device sutured onto the lung, with one of the two transmural, single lung venous cannulas shown (indicated by arrow). FIG. 8C is a close-up macroscopic image detailing transmural perforation of biologic cuff device. An optional 'grommet' (not shown, but position indicated by the black ring) may be used to secure position of the single lung venous cannula. FIG. 8D shows a close-up macroscopic image of the single lung venous cannula inside the pseudoatrium formed by the biologic cuff device. FIG. 8E shows a fiber optic image taken inside the biologic cuff device showing each single lung venous cannula. FIG. 8F shows a single lung venous cannula entering a single pulmonary vein. FIGS. 8G and 8H are radiographs of the lung showing the location of each single lung venous cannulation.

Figure 9A:
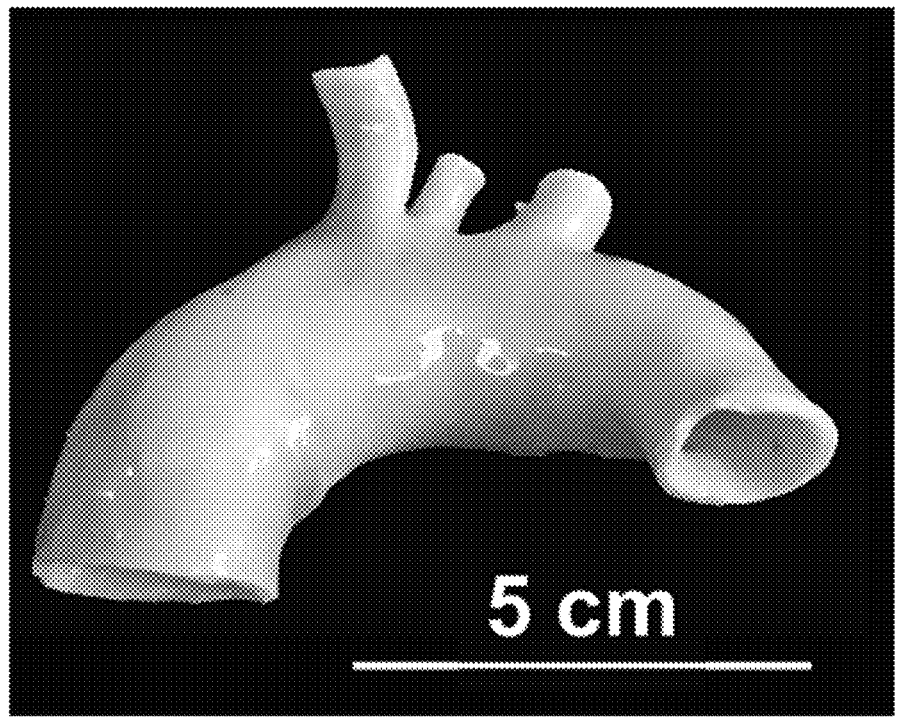
FIGS. 9A to 9E show vascular components of the biologic cuff device.
Figure 9B:
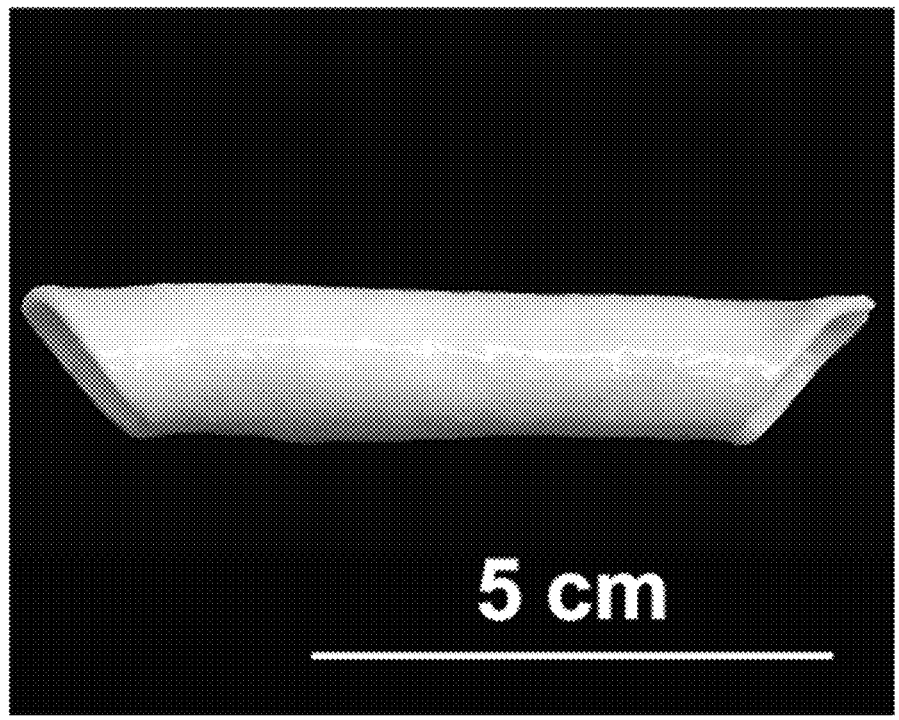
Figure 9C:
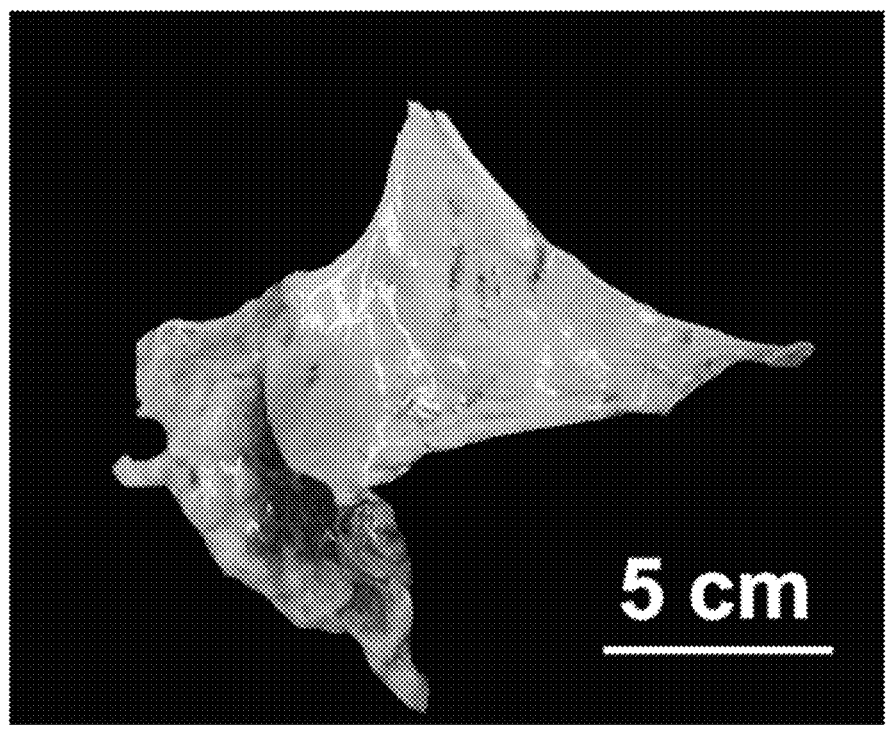
Figure 9D:
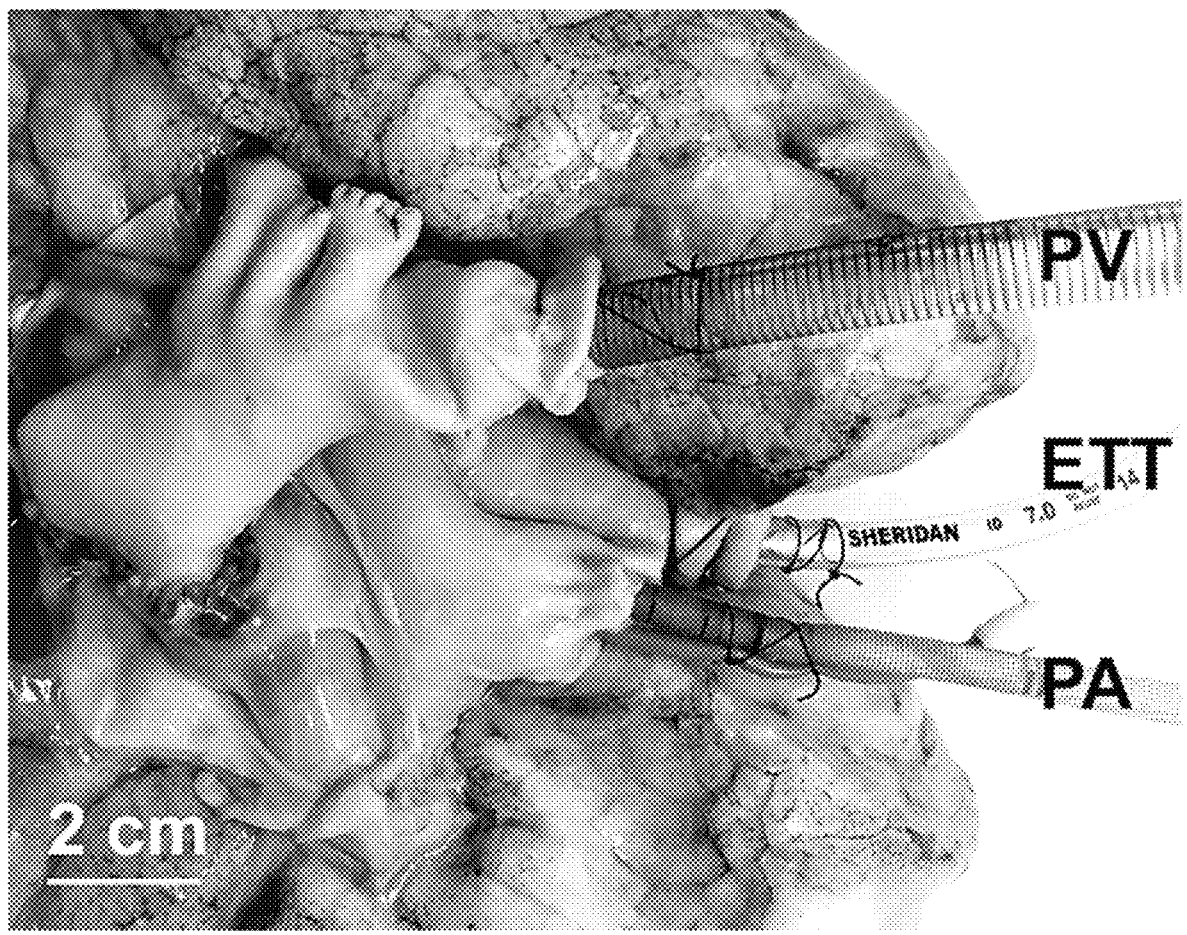
Figure 9E:
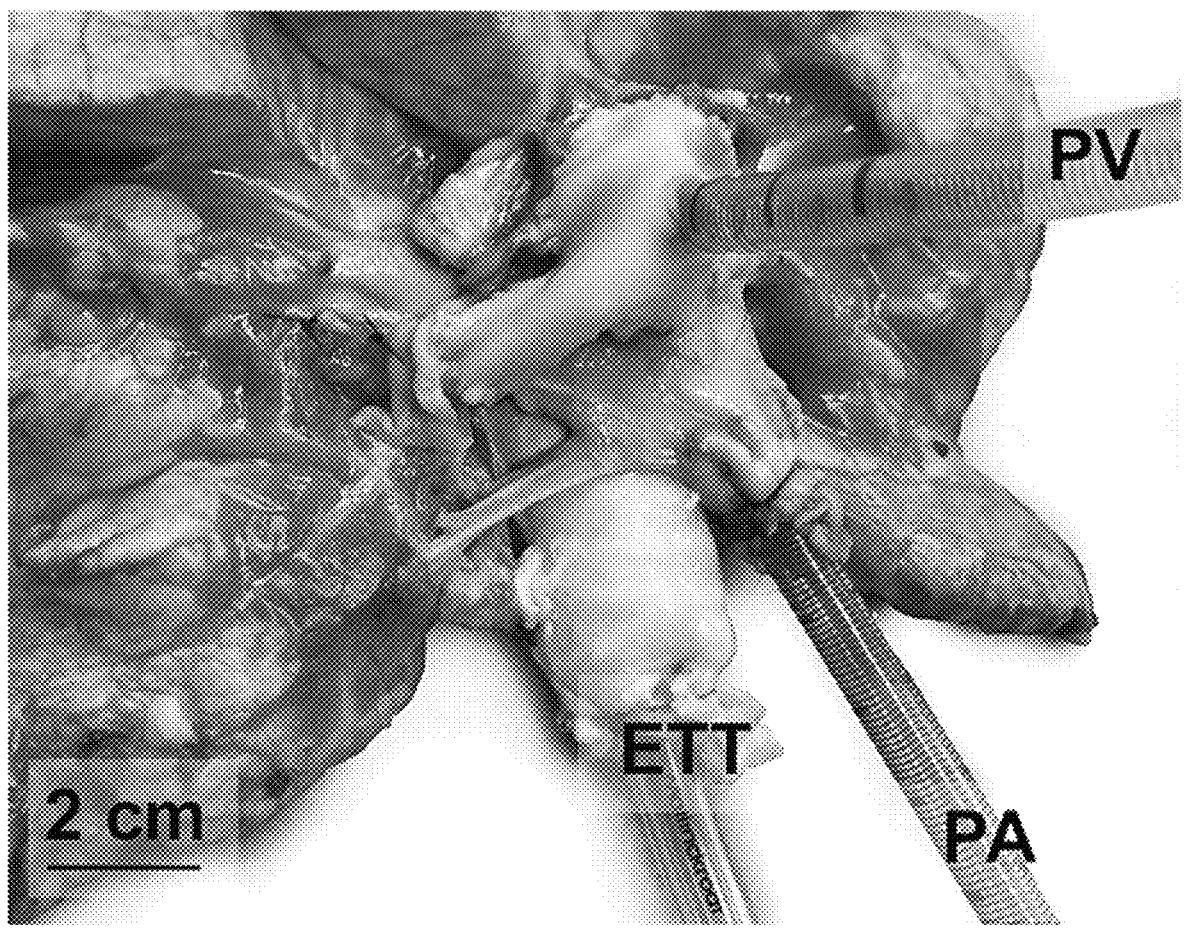

FIGS. 9A to 9E show vascular components of the biologic cuff device. Vascular components used for the biologic cuff device include the (a) aortic arch (9A), (b) abdominal aorta (9B), (c) pericardium, or superior mesenteric artery, inferior vena cava, or portal vein (9C). Cannulation of extracorporeal lungs for cross-circulation of lungs using the aortic arch is shown in FIG. 9D. Cannulation of extracorporeal lungs for cross-circulation of lungs using the pericardium is shown in FIG. 9E; ETT: endotracheal tube; PA: pulmonary artery; PV: pulmonary vein.

Figures 10A, 10B:
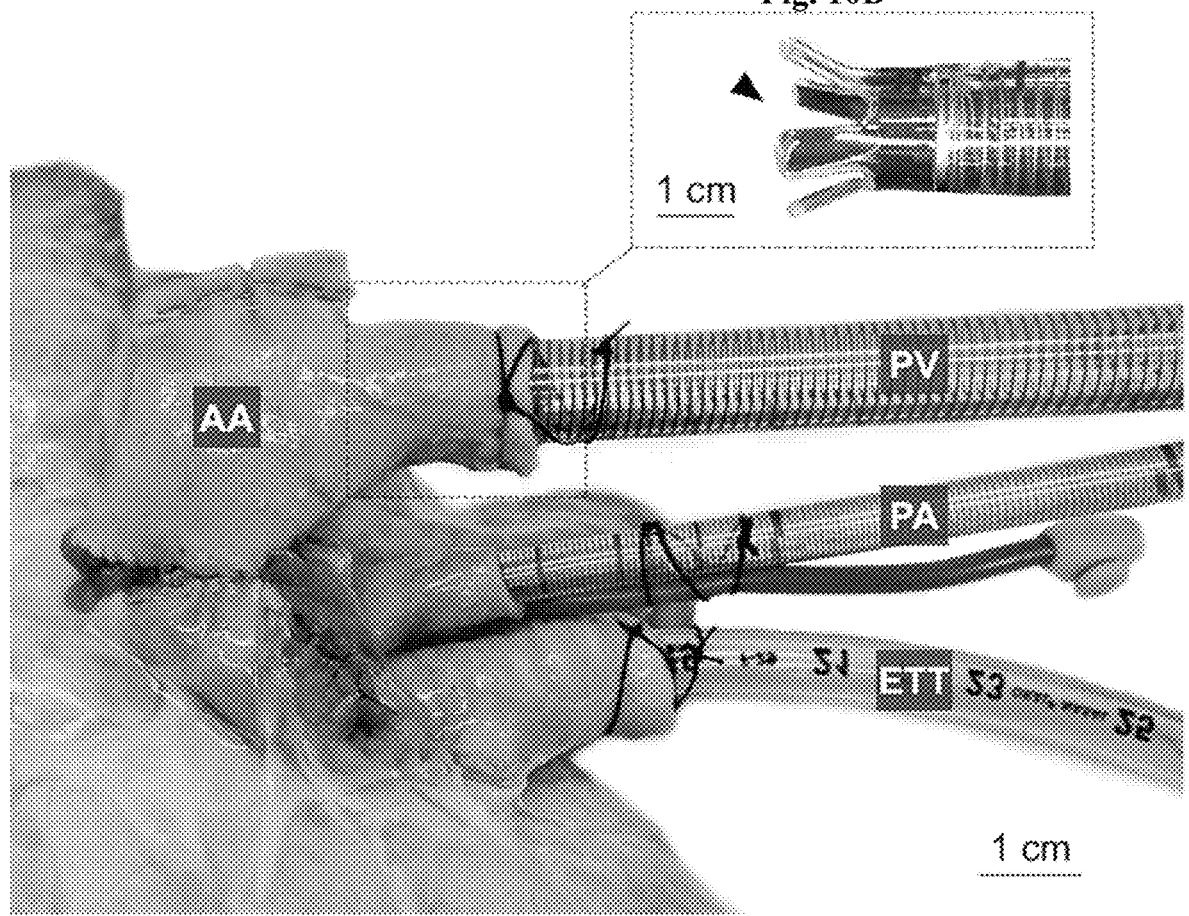
FIGS. 10A to 10C show crenellated or self-expanding stenting drainage cannulas.
Figure 10C:
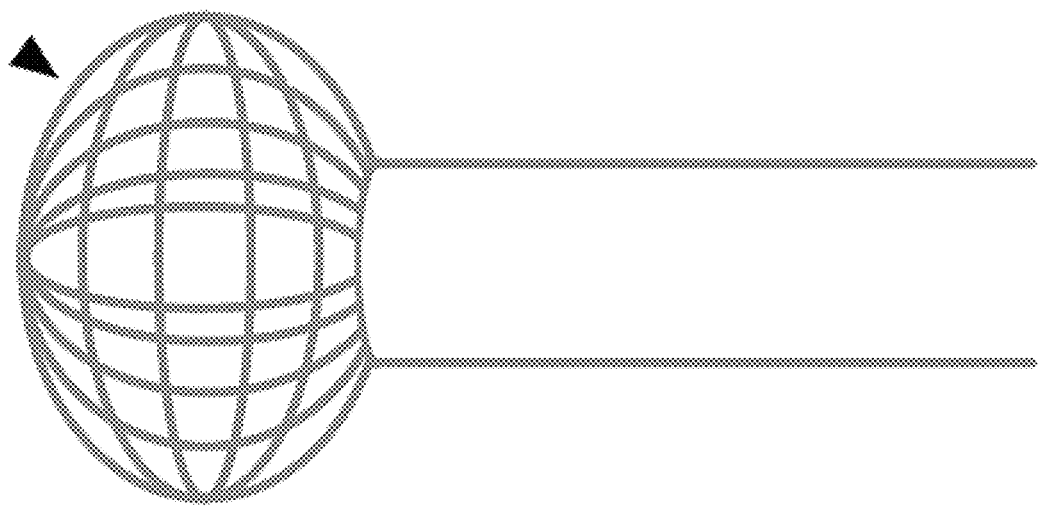

FIGS. 10A to 10C show crenellated or self-expanding stenting drainage cannulas. A venous drainage cannula with crenellations (indicated by arrow) at the tip to maintain patent lumen of vascular compartment or vessel is shown installed in the aortic arch of the biologic cuff (FIG. 10A.) and uninstalled (10B). FIG. 10C shows a schematic of a cannula with an expandable, rounded, unfolding, self-expanding, fenestrated tip (indicated by arrow) to 'stent' open venous drainage compartments, made of nitinol or other biocompatible materials. ETT: endotracheal tube; PA: pulmonary artery; PV: pulmonary vein.

FIG. 11 shows a schematic of a cross-circulation circuit comprising patient safety clamps regulated by feedback from circuit pressure sensors, flow sensors, and bubble detectors. The clamps are capable of occluding blood and/or plasma flow, effectively isolating the recipient from the extracorporeal circuit, to protect the safety of the patient in the event of the detection of unsafe pressures, flows, or bubbles in the extracorporeal circuit. The clamps may be configured on the outside of the flexible tubing or fluid conduit of the cross-circulation circuit to squeeze or pinch the tubing to occlude blood and/or plasma flow. Alternatively the clamping function may be achieved by valves in the fluid conduit. The clamps are preferably operated automatically by actuators controlled by electronic processor(s) that determines whether an unsafe condition occurs by processing signals from the sensors. The processor may be configured to report conditions in the cross-circulation circuit to a remote device such as a computer or database. The processor may also comprises an alerting function such as an alarm to indicate to a practitioner that the safety clamp has been activated.

In some embodiments, certain components of the organ chamber, perfusion circuit, cart/stand and/or the safety clamp may be aggregated into a single compound device. For example, components of the organ chamber, perfusion circuit, cart/stand and/or the safety clamp that do not come in direct contact with the host or recipient, the extracorporeal organ or blood or plasma may be combined. Such components may include heaters, coolers, temperature regulators, pumps, ventilators, sensors, water recirculation conduits, monitoring equipment, control equipment, electronics, processors, video displays, imaging devices. scales, clamps, valves and/or the like that provide the "infrastructure" of the system.

In some embodiments certain components of the organ chamber, perfusion circuit, biological cuff and/or the safety clamp may also be combined in a kit. For example, components of the organ chamber, perfusion circuit, biological cuff and/or the safety clamp that come into direct contact with the host or recipient, the extracorporeal organ or blood or plasma may be combined. These elements could be considered as single-use and/or disposable items. Such elements may include tubing, cannulae, sensor probes, filters, valves, organ chamber liners, bladders, connectors, grommets, fittings, fluid reservoirs and/or the like.

Pre-Clinical Swine Model of Cross-Circulation.

We investigated the use of cross-circulation between a recipient and an extracorporeal lung via two experimental groups: (1) a prolonged maintenance group to assess the feasibility of performing normothermic extracorporeal organ support for long enough to enable therapeutic intervention and (2) an ischaemic recovery group to demonstrate the recovery of injured lungs in a clinically relevant model. Lungs were explanted and, before cross-circulation, they were subjected to either isolated EVLP (prolonged maintenance group) or static cold ischaemia (ischaemic recovery group). The table shows timelines of prolonged maintenance and ischaemic recovery experimental groups.

|  | Time in phase (hours) | |
| --- | --- | --- |
|  | Prolonged Maintenance | Ischaemic Recovery |
| Explant | 2 | 2 |
| Cold Ischaemia (4° C.) | — | 18 h |
| EVLP | 1-4 | 1 |
| Cross circulation (30-40° C.) includes periods for | 36 | 36 |
| 1) Recovery and Assessment | 24 | 24 |
| 2) Therapeutic intervention | 12 | 12 |
| Total Extracorporeal Preservation Time | 42 | 56 |

Donor lungs were collected in the standard fashion, and the pulmonary artery (PA), pulmonary vein (PV) and trachea were cannulated as shown in FIG. 7C. The challenge of collecting venous return from multiple pulmonary veins following removal of the left atrium (FIG. 7B) was managed via the implementation of a vascular bio-bridge (7E) and a custom crenellated cannula (FIG. 10B). In the prolonged maintenance group, a conventional EVLP circuit was primed with donor blood collected during lung harvest, and EVLP was initiated. In the ischaemic recovery group, lungs were maintained at 4° C. for 18 h before initiation of EVLP. In both experimental groups, a recipient swine was placed under general anaesthesia, and the internal jugular veins were cannulated and connected to the EVLP circuit to achieve cross-circulation between the recipient and the extracorporeal lung. After 24 h of normothermic cross-circulation support, multiple experimental interventions were demonstrated until procedures were terminated as planned at 36 h of cross-circulation support.

Target parameters were defined for extracorporeal lung perfusion and ventilation for both experimental groups. Extracorporeal lung perfusion and ventilation target parameters include: PA pressure, <20 mmHg; PV pressure, 3-5 mmHg; flow, 0.2-0.4 lmin$^{-1}$ (5-10% of cardiac output); temperature, 36-38C; respiratory rate, 6-8 bpm; fraction of inspired oxygen (FiO$_2$), 40%. FIG. 6B shows the use of height differences to modulate extracorporeal blood flow (arrows) by circuit hydrostatic pressure differences. Integrated circuit elements (FIG. 2A) enabled real-time monitoring and maintenance of pressure, flow and temperature. In addition to feedback-regulated pressure-limited flow, modulation of the trans-pulmonary pressure gradient was achieved by precisely maintaining hydrostatic pressures by regulating the heights of the lung, blood reservoir and recipient. Thermal imaging confirmed that warm, freshly explanted lungs placed on ice were efficiently cooled with cold flush (in keeping with standard transplantation protocol, and warmed to normothermia following reperfusion after transfer to the warm, humidified organ chamber.

Haemodynamic Stability of the Recipient.

Haemodynamic stability was observed by measuring heart rate (bpm), systolic blood pressure (mm Hg), temperature (° C.), and SpO$_2$ (%). FIGS. 3A to 3E show aspects of recipient safety and stability throughout 36 h of cross-circulation support. Haemogas pH, p02 (mm Hg), pCO2 (mm Hg) and and HCO$_3$ (mM). Biochemical analysis included measurement of white blood cells, platelets Hemoglobin/Hematocrit levels, aspartate transaminase, alanine transaminase, lactate and glucose. Haemolytic markers measured included lactate dehydrogenase, activated clotting time, D-dimer, fibrinogen and plasma-free haemoglobin. Pro-inflammatory markers included IL-1β, IL-6, IL-8, IL-17 TNFα and Angiotensin II. Anti-inflammatory markers included IL-10 and activation markers P-selectin and M30 were also measured for recipients during prolonged maintenance and ischaemic recovery. No significant changes ($p > 0.05$) in serum levels of pro- or anti-inflammatory cytokines or activation markers were detected between 0 and 36 h of cross-circulation for recipients in the prolonged maintenance or ischaemic recovery groups.

The median weight of recipient animals (n=6) was 41.4 kg (range: 38.0-70.4 kg). Recipients were under general anaesthesia for an average of 40.1±1.5 h. All recipients remained haemodynamically stable throughout the duration of cross-circulation support, in normal sinus rhythm, and without the need for vasopressor support. There were no significant differences between the respective baseline and end-point values for lactate (1.52±0.49 mM and 0.71±0.31 mM), pH (7.48±0.07 and 7.36±0.05), or the oxygen partial pressure, pO$_2$ (530±62 mmHg and 520±81 mmHg). Haemolytic markers (lactate dehydrogenase, D-dimer, fibrinogen, plasma free haemoglobin) remained within normal ranges. Within each experimental group, no significant changes in serum levels of pro- or anti-inflammatorycytokines were detected between 0 and 36 h of cross-circulation. P-selectin, an indicator of platelet activation and endothelial injury, remained in the normal range throughout the entire procedure for both groups. M30, a marker of epithelial cell death, did not increase significantly in either experimental group. Pro-inflammatory cytokine levels were initially higher in the ischaemic recovery group and, with the exception of interleukin 1β (1β) and tumor-necrosis factor-α (TNFα), trended downward over time (IL-6, IL-8, IL-17, angiotensin II). Although elevated in the ischaemic recovery group, all cytokine levels were within previously reported normal ranges. While the anti-inflammatory cytokine IL-10 increased over the first 12 h of cross-circulation before trending downward in the prolonged maintenance group, IL-10 levels were initially higher and remained elevated throughout the 36 h of cross-circulation in the ischaemic recovery group.

Extracorporeal Lung Performance.

The percentage change of extracorporeal lung weight was monitored throughout cross-circulation procedure. Transpulmonary pressure gradient (TPG), the difference between PA and PV pressures was measured. Pressure volume loops during prolonged maintenance and ischaemic recovery were measured. Dynamic compliance (ml cmH$_2$O$^{-1}$) during prolonged maintenance and ischaemic recovery was monitored. Clearance of lactate over 36 h of cross-circulation (XC) was observed. Lactate accumulated over the course of 1, 2 and 4 h of EVLP before initiation of cross-circulation. Lactate was cleared within 12 hours of cross circulation perfusion. PaO$_2$/FiO$_2$ ratios during prolonged maintenance and ischaemic recovery were used to assess the functional capacity of the lungs to oxygenate. The oxygenation ratios were well above the threshold for mild to moderate or severe Acute Respiratory Distress Syndrome (ARDS). Blood sampling before and after extracorporeal lung performance challenges, which were defined by adjustments made to ventilation (100% FiO2 and 2× minute ventilation) every 4 h for 10-min periods was used to assess changes in pO$_2$ and pCO$_2$ in blood entering and exiting the extracorporeal lung. Responses in ΔpO2 (4H) and ΔpCO2 (41) to 10-minute challenges during prolonged maintenance and ischaemic recovery were measured.

Lung weight in the prolonged maintenance group did not change significantly (0 h, 0.48±0.09 kg; 36 h, 0.43±0.04 kg; $p > 0.05$), whereas lung weight in the ischaemic recovery group decreased significantly over the first 4 h of cross-circulation (0 h, 0.70±0.05 kg; 4 h, 0.53±0.08 kg; $p < 0.05$) and then remained stable over the remaining 32 h (4 h, 0.53±0.08 kg; 36 h, 0.57±0.04 kg; $p > 0.05$). The transpulmonary pressure gradient was tightly maintained at 5-15 mm Hg throughout all procedures. No significant changes in pressure-volume loops or dynamic compliance were observed over 36 h of cross-circulation support in the prolonged maintenance group. However, in the ischaemic recovery group, derangement in pressure-volume loops and a corresponding decrease in dynamic compliance was seen at 12 h, followed by normalization of pressure-volume loops by 24 h and compliance values exceeding those at baseline by 36 h. Notably, the build-up of lactate that occurred during the initial EVLP phase (before initiation of cross-circulation) of each experiment in the prolonged maintenance group (1.85 mM at 1 h, 8.20 mM at 2 h and 12.38 mM at 4 h) quickly normalized (<2.5 mM) following initiation of cross-circulation and remained within the normal range. In the prolonged maintenance group, extracorporeal lungs kept at a fraction of inspired oxygen (FiO$_2$) of 40% maintained a partial pressure arterial oxygen (PaO$_2$) of 315±34 mmHg corresponding to a $PaO_2/FiO_2$ (P/F) ratio of 821±102 mmHg. In the ischaemic recovery group, lungs had an initial average $PaO_2$ of 245.6±133.7 mmHg corresponding to a P/F ratio of 614.16±334.30 mmHg. Following an initial increase, all lungs experienced a slight decline in function until normalizing after 18 h. In response to the performance challenges of (1) increasing minute ventilation by 100% and (2) increasing FiO2 from 40% to 100%, extracorporeal lungs demonstrated the ability to exchange gas as shown by differences (Δ) in baseline and challenge levels of pulmonary artery and vein haemogases: ApO2 (oxygenation) and ΔpCO2 (ventilation). Notably, lungs in the ischaemic recovery group did not achieve ΔpO2 and ΔpCO2 values equivalent to lungs in the prolonged maintenance group until after 24 h of cross-circulation.

Extracorporeal Lung Analysis: Prolonged Maintenance Group.

The macroscopic appearance of extracorporeal lungs throughout cross-circulation procedure remained stable. Airway bronchoscopy at baseline and 36 h endpoint showed no apparent changes. Baseline and 36 h H&E staining (i, ii), scanning electron microscopy (iii), and transmission electron microscopy (iv) with intact type I and II pneumocytes and capillaries was determined and showed no obvious changes. The 36 h endpoint special or immunostaining included using pentachrome, trichrome, silver reticulin, Alcian blue, pan-cytoaeratin and elastic von Gieson. Metabolic activity of extracorporeal lung showed an increase from about 0.05 OD per ng DNA to about 0.18 over 24 h of cross-circulation; $*p<0.001$. Functional analyses at 36 h endpoint showed uptake of bronchoscopically delivered BODIPY-SPB by type II pneumocytes. Uptake of acetylated LDL by pulmonary arterial endothelial cells carrying the CD31 antigen was monitored, including by H&E staining and CD31 staining. Extracorporeal lung vasoresponsiveness following administration of epinephrine (epi) into the pulmonary artery after 36 h of cross-circulation was measured. The integrity of microvascular endothelium was determined by CD31 staining and tight junctions by ZO-1 staining. Neutrophils were imaged by neutrophil elastase immunostaining, early apoptosis was imaged by caspase-3 immunostaining, and late apoptosis was imaged by TUNEL staining. Macrophage quantification was determined by CD163 immunostaining; $*p<0.01$.

Donor lungs showed no apparent visual or bronchoscopic evidence of oedema. Histologic analysis, scanning and transmission electron microscopy revealed intact structural and cellular architecture in extracorporeal lungs after 36 h of cross-circulation support. Histologic staining revealed maintenance of important lung structures, including intact pseudostratified, columnar and cuboidal respiratory epithelium; airway cilia; and submucosal glands, air-way cartilage and smooth muscle; without signs of interstitial oedema or degradation of reticular or elastic fibers in the perialveolar extracellular matrix. Conducting airways were free of oedema and secretions, as observed by bronchoscopy after the 36 h of cross-circulation.

Assessment of extracorporeal lung metabolism showed a significant increase in metabolism over the first 24 h of cross-circulation support. The viability and function of type II pneumocytes was confirmed by uptake of boron-dipyrromethene-labelled surfactant protein B (BODIPY-SPB) delivered into the distal lung. Function of the pulmonary endothelium was confirmed by uptake of acetylated low density lipoprotein (LDL) in pulmonary arterial endothelial cells.

Vascular integrity was demonstrated by transmission electron microscopy analysis of small vessels. CD31 immunostaining confirmed preservation of the pulmonary microvasculature, and immunostaining for tight junction protein 1 (ZO-1) confirmed retention of tight junction proteins in pulmonary capillaries and microvessels. Increases by 6-9 mmHg in pulmonary artery and vein pressures were measured in response to epinephrine bolus at 36 h to confirm preservation of vasoresponsiveness to adrenergic stimulation.

Pathologic assessment of the extracorporeal lung was performed in a randomized blinded fashion to obtain lung injury scores. Extracorporeal lungs were scored by quantification of marginalized neutrophils, early and late apoptotic cells, alveolar oedema and interstitial infiltrate. Scores in individual categories were added to obtain composite lung injury scores at 0, 12 and 24 h of cross-circulation. There were no significant differences between the 0, 12 and 24 h time points in either individual or composite lung injury scores. To assess the immune response in the distal lung, interstitial and alveolar macrophages were quantified, and a significant decrease in those carrying the CD163 antigen ($p<0.001$) was found between initiation and 24 h of cross-circulation.

Extracorporeal Lung Analysis: Ischaemic Recovery Group.

Macroscopic analysis of injured lungs included observation of gross appearance, X-ray and thermal images throughout cross-circulation procedure. Analysis of pulmonary airways was done by bronchoscopy. Myeloperoxidase (MPO) activity in injured lungs was monitored throughout cross-circulation procedure; $*p<0.001$. Cells in BAL fluid at 0 h (upper) and 36 h (lower) were observed using Kwik-Diff staining. Metabolic activity of extracorporeal lungs during prolonged maintenance and ischaemic recovery; $*p<0.001$ was observed. Transmission electron microscopy of injured lungs at 0, 12 and 36 h of cross-circulation was performed. Denuded alveolar basement membrane was observed at 0 and 12 hours. Pulmonary microvasculature at 0, 12 and 36 h of cross-circulation was observed using ZO-1 (tight junction protein1) immunostaining. Lung injury scoring on alveolar and interstitial areas was performed. Macrophage Quantification used CD163 immunostaining; $*p<0.01$. Microscopic airway analysis of injured lungs after 36 h of cross-circulation used Alcian blue staining of secretory airway submucosal glands, pentachrome staining of intact columnar airway epithelium and airway cilia, and scanning electron microscopy of airway cast of injured lungs after 36 h including bifurcating bronchiole and alveolar sacs. Function and integrity of type II pneumocytes was determined by uptake of BODIPY-SPB at 36 h. and transmission electron microscopy of secretory organelles and intact microvilli in a single type II pneumocyte. Integrity of the pulmonary airway epithelium of injured lungs after 36 h of cross-circulation was observed by viability (CFSE), maintenance of pulmonary neuroendocrine cells (PGP9.5) and barrier function by alveolar epithelial tight junction protein 3 (ZO-3). Analysis of extracorporeal lung vasculature included testing of vasoresponsiveness following administration of epinephrine into the pulmonary artery after 36 h of cross-circulation. Vascular integrity was shown by X-ray following administration of radiocontrast dye. Smooth muscle actin (SMA) immunostaining showed intact muscular layers surrounding vessels and airways. Uptake of CSFE by pulmonary artery endothelial cells confirmed viability of the endothelial lining after 36 h.

Following 18 h of cold ischaemia, lungs demonstrated gross, radiographic and thermographic evidence of consolidation, atelectasis and non-uniform perfusion. Bronchoscopy at the initiation of cross-circulation revealed mild airway oedema and abundant cellular content in bronchoalveolar lavage (BAL) fluid. By 24 h of cross-circulation, airway oedema resolved, atelectatic lung was recruited, and lungs were uniformly perfused and remained normal up to 36 h, at which time fewer cells were observed in the BAL fluid. Myeloperoxidase activity, an indicator of neutrophil activation, was elevated at 12 h but was significantly reduced by 36 h (p<0.001). Histologic analysis revealed neutrophil migration and extravasation into the interstitial space surrounding vessels and large airways from 0-12 h, with resolution by 36 h. Following ischaemia-reperfusion, metabolism of extracorporeal lungs significantly increased over 24 h. Microscopic analysis revealed derangements in lung architecture at 0, 6 and 12 h, and intact structural and cellular architecture at 24 and 36 h. Transmission electron microscopy showed denuded basement membrane with gaps between type I pneumocyte cell membranes at 0 and 12 h. By 24 and 36 h, the alveolar blood-gas barrier was shown to be intact. A decrease in ZO-1 was observed at 0 and 12 h, with recovery by 36 h. At 36 h, ZO-1 staining was similar to that in healthy lungs. Randomized blinded pathologic lung injury scoring revealed a significant decrease in the composite lung injury score at 24 h. Quantification of macrophages carrying CD163 revealed a significant decrease in the total number of interstitial and alveolar macrophages between 12 and 24 h (p<0.001). Compared with lungs in the prolonged maintenance group, lungs in the ischaemic recovery group received higher composite lung injury scores at 0 and 12 h, with no difference in composite injury scores between the groups at 24 h.

Integrity of the pulmonary epithelium was assessed after 36 h of cross-circulation. Alcian blue staining and scanning electron microscopy of airway casts confirmed the maintenance of a large-airway, bronchiolar and alveolar architecture, pseudostratified epithelium, and secretory function of submucosal mucous glands. Pentachrome staining revealed the presence of fully intact ciliated brush borders in large airways. Live imaging of airway biopsies demonstrated viable cilia with coordinated beating, confirming functional preservation of the mucociliary escalator after 36 h of cross-circulation. Type II pneumocytes were visualized by transmission electron microscopy, and their viability and function at 36 h was confirmed by the uptake of fluorescently labelled BODIPY-SPB. Viability of pseudostratified epithelium in large airways was confirmed by the uptake of bronchoscopically delivered carboxyfluorescein succinimidyl ester (CSFE) at 36 h. Immunostaining for protein gene product 9.5 (PGP9.5) demonstrated maintenance of pulmonary neuroendocrine cells, and epithelial tight junction protein 3 (ZO-3) immunostaining suggested intact barrier function after 36 h of cross-circulation. The pulmonary vasculature was visualized by the injection of a radiocontrast dye at 36 h. Viability of pulmonary arterial endothelial cells was confirmed by the uptake of CSFE, and smooth muscle actin immunostaining showed preservation of airway and vascular smooth muscle after 36 h of cross-circulation. Increases by 9-15 mm Hg in pulmonary artery and vein pressures were measured in response to an epinephrine bolus at 36 h, confirming vasoresponsiveness to adrenergic stimulation in a manner consistent with lungs in the prolonged maintenance group.

Assessment of Airway Inflammation.

Analysis of BAL fluid inflammatory markers during prolonged maintenance and ischaemic recovery was conducted. Delivery and uptake of a cell viability marker (CFSE) in target regions of the distal lung was determined. No uptake was observed in blood vessels (bv), interstitium (int) or non-targeted proximal airways (aw). Transpleural imaging setup allowed for non-invasive in situ imaging of microbeads and stem cells delivered to distal lung. Transpleural imaging following therapeutic delivery of microbeads and mesenchymal stem cells (MSCs) was conducted and histologic analysis of delivered MSCs was performed. Global distribution of MSCs throughout lung was observed. MSCs delivered in single cell suspension were localized in alveoli and interstitium. MSCs delivered in aggregate clusters, co-localized with integrin-β 1. Histologic comparison of native and de-epithelialized lung using H&E staining showing removal of pseudostratified and squamous epithelium in conducting airways and alveoli, with retention of intact pulmonary vasculature. Pentachrome stain showed preservation of airway and alveolar basement membrane and extracellular matrix components including glycosaminoglycans (GAG), collagen and elastic fibers in de-epithelialized regions. Cell replacement by targeted delivery of airway epithelial cells (AEC) into large airways was performed using a lung matrix hydrogel carrier, and lung stem cells (LSC) into alveoli.

To assess the effect of cross-circulation on airway inflammation, BAL fluid was analyzed for total protein and the inflammatory markers, interferon γ (IFNγ), IL-1β, IL-6, IL-8, IL-10, IL-17, M30 and TNFα. IFNγ was not detected at any time point in either experimental group. In the prolonged maintenance group, markers with no significant changes over 24 h of cross-circulation were total protein, IL-6 and M30. Significant increases were measured for IL-8 and IL-10, and significant decreases were measured for IL-1β, IL-17 and TNFα over 24 h of cross-circulation. In the ischaemic recovery group, total protein and inflammatory cytokine levels were initially higher relative to the prolonged maintenance group, with the exception of IL-17. Total protein, IL-6, and TNFα increased significantly from 0 to 12 h and subsequently decreased significantly between 12 and 24 h.

Demonstration of Multiscale Interventions in Extracorporeal Lungs.

Multiscale interventions in extracorporeal lungs were demonstrated. After 36 h of cross-circulation, a fluorescent cell viability marker (CFSE) was delivered with bronchoscopic guidance to targeted regions of the distal lung. Uptake of CFSE observed in all target regions confirmed cell viability at 36 h and demonstrated the potential for targeted delivery of therapeutics into the extracorporeal lung during cross-circulation.

The size of commercially available bronchoscopes limits their ability to access and visualize the distal lung. Because of the growing number of bronchopulmonary therapeutics and the need to measure improvements in lung function, we developed a compact transpleural imaging system that enabled non-invasive, real-time surveillance of the lung and guided delivery of microbeads and fluorescently labelled porcine mesenchymal stem cells (MSCs) to the distal lung. Labelled MSCs were widely distributed throughout targeted regions of lung and clearly seen in the alveoli and pulmonary interstitium. Post-procedural analysis of MSCs showed co-localization with integrin-β1, an adhesion molecule known to mediate the migration of MSCs into the interstitium in multiple tissues.

To demonstrate the feasibility of replacing lung epithelium during cross-circulation, targeted bronchopulmonary segments were decellularized by micro-catheter delivery of 3-[(3-Cholamidopropyl) dimethylammonio]-1-propanesulfonate (CHAPS), a reagent previously used for lung decellularization. Histologic comparison of intact and de-epithelialized airways confirmed the removal of epithelium in large airways and alveoli, without disruption of adjacent large arteries, microvasculature or capillaries. Pentachrome staining suggested retention of extracellular matrix proteins including collagens and glycosaminoglycans, critical structural and biochemical factors for the proper attachment and function of newly delivered cells. The absence of haemorrhage, oedema and necrosis suggests that the regional decellularization process was well tolerated, and the stability and performance of the lung was unaffected. Decellularization was followed by delivery of pulmonary epithelial cells: heterogeneous populations of small airway epithelial cells and embryonic-stem-cell-derived alveolar progenitor cells were delivered to the large airways and distal alveoli, respectively, to replace the cells removed by decellularization. Small airway epithelial cells, delivered in a hydrogel made of lung extracellular matrix, were distributed across the airway surface and attached to the denuded basement membrane, while alveolar progenitors were observed throughout the alveoli.

This first application of cross-circulation as a platform for prolonged normothermic extracorporeal organ support resulted in (1) the maintenance of viable extracorporeal lungs and stable recipients after 36 h of cross-circulation, and (2) the recovery of lungs subjected to ischaemia reperfusion injury.

The cross-circulation platform provided important benefits to the extracorporeal lung, and significantly extended the duration of normothermic support beyond what is currently achievable with EVLP. Recently published reports of prolonged preservation times include periods of cold ischaemia, and normothermic perfusion remains limited to a mean of $5.00±0.93$ h, with a mean total preservation time of $14.60±1.82$ h. In the present study, we demonstrate that normothermic perfusion (EVLP +cross-circulation) can be extended to $37.67±1.21$ h, with total preservation time (cold ischaemia+normothermic perfusion) extending to $56.24±0.11$ h. Although cross-circulation support was terminated at 36 h to adhere to prescribed animal protocols, we postulate that cross-circulation could be extended to days or even weeks, an assumption currently being tested. Prolonging the duration further would allow for advanced therapeutic interventions not currently feasible; for example, gene/stem cell therapy, targeted cell removal/replacement, airway microbiome manipulation, bacterofection and donor-recipient immune modulation. Cross-circulation could serve as a platform for the recovery of organs that are unacceptable for transplantation, and could enable the assessment of graft function and modulation of the recipient response. This capability would allow for early recognition of primary graft dysfunction and for interventions prior to transplantation. Because this platform allows for continuous organ and recipient monitoring, it is well suited for studies of lung physiology, immunology and xenotransplantation.

Establishment of cross-circulation required the development of strategies to address challenges unique to prolonged extracorporeal organ support. Pulmonary venous drainage was managed using an endothelialized (that is, non-thrombogenic) bio-bridge between the pulmonary veins and the extracorporeal circuit, offering several key features as an alternative to artificial cuffs and gravity collection systems. Pressure-limited flow allowed tight maintenance of a physiologic trans-pulmonary pressure gradient of between 5 and 15 mmHg throughout the duration of extracorporeal support, while height differences allowed for modulation of PV pressures via hydrostatic pressure differentials.

In this study, the prolonged maintenance group consisted of healthy lungs that (1) served as proof that cross-circulation could support lungs outside the body at normothermia while preserving cell viability and global function for 36 h and (2) established recipient safety. In addition, lungs in the prolonged maintenance group served as healthy controls providing baseline values and trends over time for uninjured lungs on cross-circulation. To assess the ability of cross-circulation to recover damaged lungs in a clinically relevant injury model, lungs were subjected to ischaemia reperfusion injury followed by 36 h of cross-circulation (ischaemic recovery group). Lungs in the ischaemic recovery group were subjected to 18 h of static cold ischaemia, a period that is two to three times longer than what is accepted by most centers. Histologic evidence of cell and tissue derangement as a result of cold ischaemia was observed in separate injury validation studies and confirmed in blinded pathologic assessment of injured lungs.

Inflammation was assessed by analysis of inflammatory cytokines in the serum and BAL fluid. For markers of inflammation, lung pathologic scoring, lung metabolism and macrophage quantification, our analyses included time points up to 24 h to assess the effects of cross-circulation alone before any intervention in the extracorporeal lung (for example, decellularization and cell replacement). Preservation of lung integrity and function was demonstrated in the prolonged maintenance group throughout the entire duration of cross-circulation. For recipient serum markers, there were no significant differences over 24 h of cross-circulation, underscoring the maintenance of homeostatic stability. Notably, BAL fluid analysis in the extracorporeal lung demonstrated a significant increase in anti-inflammatory IL-10 and significant decreases in pro-inflammatory IL-1$\beta$ and IL-17. TNF$\alpha$ did not decrease significantly until after 12 h of cross-circulation, highlighting the value of prolonged recovery time. Although IL-8 increased, endpoint concentrations were 6-400 times lower than previously reported values.

In the ischaemic recovery group, lung weight and airway oedema were significantly reduced after 4-6 h of cross-circulation support (results that would be expected with an equivalent duration of EVLP. However, a downward trend in several indicators of lung quality and function, such as dynamic compliance, P/F ratio and ZO-1, continued to decline in the first 12 h of cross-circulation before recovering to baseline values by 24 to 36 h; thus highlighting the developmental nature of reperfusion injury and the importance of prolonged support time to enable recovery. Reperfusion injury is partly initiated by activated macrophages known to play a role in surfactant degradation and in the rapid release of cytokines, most notably TNF$\alpha$. In the ischaemic recovery group, alveolar macrophages were highest at 12 h, corresponding to a decrease in lung compliance and a significant increase in BAL levels of TNF$\alpha$ at the same time. By 24 h macrophages and TNF$\alpha$ levels were significantly decreased, and compliance improved.

Neutrophils perpetuate the late phase of reperfusion injury (after 4 h of reperfusion) by increasing oxidative stress. In the ischaemic recovery group, the increased presence of marginated neutrophils between 0 and 12 h, and the subsequent decrease between 24 and 36 h, was confirmed by haematoxylin and eosin (H&E) staining and blinded pathologic assessment, quantified by neutrophil elastase immunostaining, and assessed via myeloperoxidase activity. Furthermore, decreased ventilatory function, blinded pathologic assessment, analysis by transmission electron microscopy and reduced ZO-1 immunostaining all indicated that cellular derangement occurred throughout the first 12 h.

Beyond 12 h of cross-circulation, injured lungs recovered cellular and structural integrity and showed significant improvements at the cell and tissue level as well as in global function. Comprehensive analyses of recovered lungs revealed the following: gross appearance, radiography and thermography consistent with healthy lungs; absence of airway secretions, and interstitial and alveolar oedema; restoration of barrier function with intact alveolar epithelium and epithelial and vascular tight junctions; recovery of cellular and structural integrity that was histologically consistent with healthy lungs; maintenance of airway structures including cartilage, smooth muscle and submucosal glands; and viability and function of the mucociliary escalator, pulmonary epithelial cells and vascular endothelial cells. Taken together, these data underlie a global lung function that resulted in P/F ratios >800 mmHg (values similar to those in healthy lungs) after 56 h outside the body.

Beyond prolonged normothermic extracorporeal support, cross-circulation may also enable interventions not currently feasible ex vivo. Targeted micro-volume delivery techniques and the development of a radiation-free, real-time transpleural imaging systems enabled directed region-specific interventions rather than whole lung decellularization or treatment strategies. We demonstrated global, single-lobe and subsegmental delivery and engraftment of MSCs in both single-cell and aggregate suspensions. Given the large number of clinical trials of MSC therapy, cross-circulation may offer opportunities to improve delivery techniques and further investigate the engraftment and function of therapeutic stem cells over time.

While the use of inbred swine reduced immunological interactions enabled this initial proof-of-concept study, future work will investigate prolonged cross-circulation between unrelated donor and recipient swine kept on immunosuppression. This study investigated lungs subjected to ischaemia reperfusion injury, ongoing studies are assessing the ability of cross-circulation to rescue severely damaged lungs in a gastric aspiration model. Swine recipients were healthy at baseline. We envision that patients with end-stage lung disease on extracorporeal membrane oxygenation support awaiting lung transplantation may be candidates for clinical applications of cross-circulation. Initial candidates will probably be those with isolated lung disease (for example, interstitial lung disease) capable of handling the additional metabolic demand of an extracorporeal lung (~5% of total body metabolism). Before the implementation of cross-circulation, ethical considerations such as patient safety, informed consent, training and credentialing of providers, and outcome analysis would need to be addressed in a manner that is consistent with medical standards. While flow in the extracorporeal lung was maintained at 5-10% of cardiac output, future studies should include ramp-up strategies to reach 40% of cardiac output. Lungs maintained and recovered by cross-circulation were not transplanted. Future studies will investigate the effect of extended cross-circulation support on early and late outcomes following lung transplantation.

An intervention of increasing interest is cell replacement, whereby damaged or diseased cells are removed and replaced with healthy cell progenitors or differentiated cells. We demonstrated removal and replacement of the pulmonary epithelium in a targeted region-specific manner while maintaining the overall function and integrity of the lung. To better control cell delivery into proximal airways, a hydrogel prepared from lung extracellular matrix was used as a natural carrier of airway cells. Our novel transpleural imaging system enabled real-time visualization of cells during delivery and confirmed distribution, localization, and enabled monitoring over time without tissue sampling. Notably, this device has the potential to facilitate basic research and translational applications and to direct clinical interventions as a theranostic for image-guided delivery of therapeutic agents to distal regions of the lung not accessible by conventional bronchoscopy.

Patient-derived cell therapies offer exciting opportunities for the engineering of chimeric organs and may ultimately reduce the burden of immunosuppressive therapy and the incidence of chronic rejection. On the basis of the results reported here, we envision that cross-circulation could be applied to other transplantable organs, bioengineered grafts and xenotransplantation models.

EXAMPLES

Methods
Study Design.

The study was designed as a pilot study (n=6) for the purposes of testing procedures and demonstrating proof of concept for a 36 h cross-circulation procedure. Our hypothesis was (1) extracorporeal lungs could be maintained with cross-circulation support for 36 h and (2) lungs subjected to prolonged cold ischaemia could be recovered. The study was conducted with the minimum number of animals to achieve reproducibility and statistical significance between time points. Data from this initial study will be used to conduct power analysis for subsequent investigations. Collection of all samples was performed as technical replicates in triplicate.

Randomization of sampling. Samples of extracorporeal lung collected for histologic, microscopic, and pathologic analyses were collected randomly during procedures according to a pre-determined lung map with 16 regions arbitrarily numbered by a random number generator (http://www.random.org).

Blinded review. All analytical assessments were blinded to the maximum practical extent. Pathologic analysis was performed by an independent expert to eliminate bias.

Animals.

Twelve miniature swine (six donor-recipient pairs) were used in this study. Matched pairs of animals with well-defined major histocompatibility complex (MHC) loci were selected from a herd of partially inbred swine; selective breeding methods and detailed immunogenetic characteristics of this herd have been previously described. Animals were 5-7 months of age, with a median weight of 40.2 kg (range, 38.2-47.3 kg) in the prolonged maintenance group, and a median weight of 43.8 kg (range, 38.0-70.4 kg) in the ischaemic recovery group. The study received approval from the Institutional Animal Care and Use Committee (IACUC) at Columbia University. All animal care and procedures were conducted in accordance with the US National Research Council's Guide for the Care and Use of Laboratory Animals, 8th edition.

Donor Lung Harvest.

Donor pigs (n=6) underwent general anaesthesia via intramuscular induction with Telazol (5 mg per kg of body weight (hereafter, $kg^{-1}$); Zoetis) and buprenorphine hydrochloride (0.03 mg $kg^{-1}$; Hospira), and maintenance with continuous intravenous infusions of fentanyl citrate (0.1 mg kg$^{-1}$ h$^{-1}$; West-Ward), midazolam (1.5 mg kg$^{-1}$ h$^{-1}$; Alcorn), and inhaled isoflurane (1-5% in oxygen; Henry Schein). Cefazolin (30 mg kg$^{-1}$; WG Critical Care) was given intravenously prior to skin incision and median sternotomy.

A bolus of heparin (30,000 U) was intravenously administered (Sagent), and a cannula was placed and secured in the main pulmonary artery. Autologous blood was withdrawn and collected in citrate-phosphate-dextrose collection bags (Chinook Medical) and stored at 8° C. Once a non-perfusing rhythm was observed, a cold anterograde low-potassium dextran flush (Perfadex®, Vitrolife) with alprostadil (25 mg kg$^{-1}$; Prostin VR Pediatric, Pfizer) was administered, and the appendage of the left atrium was cut. Topical cooling was applied, the lungs were inflated to a sustained airway pressure of 15 cmH$_2$O, and the trachea was stapled (Endo GIA device; Medtronic). The heart and lungs were explanted en-bloc and placed on ice on a sterile back table.

In each donor swine, the heart was removed, leaving behind a circumferential left atrial cuff with a height of 3-5 mm. A cold retrograde flush with Perfadex® (20 ml kg$^{-1}$) was then performed. The aortic arch was dissected free and the brachiocephalic and left subclavian branches were stapled or suture ligated. A 3-4 cm section of aorta was left on either side of these vessels to facilitate placement of the PV cannula on one end and attachment to the left atrial cuff on the other.

Lung Storage for Prolonged Cold Ischaemia.

Lungs in the ischaemic recovery group (n=3) were placed in a sterile isolation bag with 500 ml of Perfadex®. That bag was then placed in a second sterile isolation bag containing 1l of normal saline and immediately placed on ice at 4° C. The median duration of cold ischaemia was 18.6 h (range, 18.1-18.95 h). Lungs in the prolonged maintenance group (n=3) were immediately cannulated and started on conventional EVLP.

Lung Cannulation and Conventional EVLP of the Donor Lung.

The aortic arch, acting as a bio-bridge, was connected to the left atrial cuff with a running 6-0 prolene suture (Ethicon), and a 36F crenellated venous drainage cannula was secured in place with a 2-0 Ti-Cron tie (Covidien). An 18-20F pulmonary artery cannula was secured in place with a purse-string 5-0 prolene suture and TourniKwik tourniquet (Medtronic). The trachea was cannulated with a 7.5 mm cuffed endotracheal tube (Sheridan). A 1l bag of cold normal saline was used to flush the lungs and remove air from inside the PA and PV cannulas. A top-loading balance (Denver Instrument Company) and a double-lined warm saline-filled organ basin were placed in the preservation chamber (XVIVO Organ Chamber; XVIVO). The lungs were then placed in the basin in prone position, and the cannulas were secured. The circuit was primed with whole blood collected during donor harvest, de-aired and connected to the extracorporeal lung. Initial flow rates were set to 5-10% of the estimated cardiac output, with a target PA pressure of <15 mmHg and PV pressure of 3-5 mmHg.

The circuit and lungs were allowed to acclimate to ambient temperature, and ventilation was initiated within the first 10 min of conventional EVLP, with the following initial settings: volume control mode; respiratory rate, 6-8 bpm; tidal volume (TV), 6-8 ml kg$^{-1}$; positive end-expiratory pressure (PEEP), 5 cmH$_2$O; and FiO$_2$, 40% (Oxylog 3000 plus; Dräger). Atelectatic lung regions were recruited by increasing TV and PEEP (up to 10 cmH$_2$O), and by performing inspiratory hold maneuvers (up to 25 cmH$_2$O). Manual recruitment was used if ventilation strategies failed to fully recruit all areas of the lung.

EVLP ranged in time from 1-4 h in the prolonged maintenance group as a demonstration of the need for homeostatic regulation. EVLP duration in the ischaemic group lasted 30-60 min. To maximize safety, vascular leaks, air entrapment or circuit problems were addressed at this stage, before connection to the recipient.

Cross-Circulation.

Recipient pigs (n=6) underwent sedation and general anaesthesia in a similar fashion to donor pigs. Cefazolin (30 mg kg$^{-1}$) was given prior to skin incision and the pig was redosed every 8 h. A femoral arterial line (Arrow International) was placed for haemodynamic monitoring and periodic blood sampling. Bilateral neck cut-downs exposed the right and left internal jugular veins. A 15,000 U heparin bolus was administered, and cannulation with 18F catheters was performed in the standard fashion using the Seldinger technique. Immediately before the initiation of cross-circulation, recipient pigs were intravenously administered 1 g of methylprednisolone (APP Pharmaceuticals) and 500 mg of calcium chloride (Hospira). Donor blood used to prime the circuit during EVLP was not removed. As shown in the circuit (Supplementary FIG. 2b,c), the tubing was spliced to connect the recipient pig to the conventional EVLP circuit, marking the start of cross-circulation.

Circuit elements consisted of a main console (Jostra HL-20 pump console; Maquet), disposable pump (Rotaflow centrifugal pump; Maquet), a soft shell reservoir (Maquet) and three-eighth inch tubing (Smart coated tubing; Livallova). Pressure (PA and PV), flow (PA and PV) and temperature data were continuously monitored and recorded (VIPER clinical interfacing software; G2 v1.26.4; Spectrum Medical). Throughout the duration of cross-circulation, the recipient was maintained on a continuous heparin infusion (initial rate of 25 U kg$^{-1}$h$^{-1}$).

Activated clotting time was measured using a HemoChron whole blood micro-coagulation system (Accriva Diagnostics), and the heparin drip was adjusted to maintain a target value of 250-350 s. Physiological parameters of the recipient, including heart rate, electrocardiogram, blood pressure (cuff and arterial A-line pressure), mean arterial pressure (MAP), oxygen saturation (SpO$_2$), end-tidal CO$_2$, temperature, and respiratory rate, were continuously monitored and recorded using a multi-parameter Advisor vital signs monitor (SurgiVet).

Blood Analysis,

Recipient monitoring. Blood samples were drawn from the femoral A-line every hour. Blood gas analysis was performed using an epoc point-of-care blood analysis system (Epocal). Additional samples were collected in test-specific specimen vials (BD Vacutainer) every 4 h and sent to the laboratory (Antech Diagnostics, New Hyde Park, N.Y., USA) for complete blood count, basic metabolic panel, liver function tests, lactate dehydrogenase, and coagulation panels. Additional haemolytic markers (d-dimer, fibrinogen, plasma free haemoglobin) and inflammatory markers (angiotensin II, IL-1β, IL-6, IL-8, IL-10, IL-17, M30, P-selectin, RAGE, TNFα and IFNγ) were analyzed using commercially available enzyme-linked immunosorbant assays (ELISAs), in triplicate, according to the manufacturer's instructions.

Extracorporeal lung monitoring. Blood samples were drawn from the PA cannula (blood entering the lungs) and PV cannula (blood exiting the lungs) every hour and analyzed in the same fashion as recipient samples. Temporary changes in ventilation settings (minute ventilation and FiO$_2$)

were made in order to further assess extracorporeal lung performance every 4 h. Immediately following this challenge period, a second set of blood samples were drawn from the PA and PV cannulas. Dynamic compliance ($C_{dyn}$=TV/(PIP-PEEP); ml per cmH$_2$O; PIP, peak inspiratory pressure) of the extracorporeal lung was calculated every 4 h. Pressure and volume recordings of the lung were measured using a custom-configured measurement system consisting of sensors and an acquisition device (Arduino Uno). Data collected via this system were processed and pressure-volume loops were generated using MATLAB v.R2016b (Mathworks). Lung weight was obtained every 4 h using a scale (Denver Instrument Company) housed inside the organ chamber. The basin and contents were tared (zeroed) at each time point to ensure accurate recordings. X-ray images of the lung were acquired using a PXP-16HF portable X-ray unit (United Radiology Systems) at 2.2 mA s and 90 kVp. A 15-20 ml injection of Optiray 320 (Medtronic) was administered to evaluate the vascular network integrity of the lung at the end of the experiment.

HAL Analysis.

Sample collection was performed by wedging a 3.8 mm flexible bronchoscope (Ambu aScope3) into a subsegmental bronchus of the right or left lung. Normal saline (10 ml) was injected twice, aspirated, and then collected in a sterile specimen trap (Busse Hospital Disposables). Specimens were centrifuged at 3,500 rpm for 10 min at 4° C. Snap-frozen supernatants were stored at −80° C. until further processing. Inflammatory markers (IL-1β, IL-6, IL-8, IL-10, IL-17, M30, P-selectin, RAGE, TNFα and IFNγ) were analyzed using commercially available enzyme-linked immunosorbant assays (ELISAs), in a similar fashion to the blood samples. BAL total protein concentrations were determined using a protein assay (Pierce Coomassie Bradford Protein Assay kit, Thermo Fisher) with bovine serum albumin as the standard. Smears of BAL fluid were allowed to dry on glass coverslips and then stained using a commercially available Shandon Kwik-Diff kit (Thermo Fisher) according to manufacturer's instructions. Slides were imaged as previously described.

Functional Assays.

Acetylated LDL uptake. To assess the vascular endothelium, at the end of each experiment, biopsies of the left and right pulmonary artery and sections of pulmonary veins were collected and placed in a 96-well plate (BD Falcon). Acetylated LDL, Alexa Fluor 594 conjugate (Thermo Fisher, L35353) was diluted 1:200 in DMEM/F12K (50/50) cell culture media (Corning). Media alone (control; 150 µl) was added to wells containing vascular biopsies from each source. The remaining wells received 150 µl of media containing acetylated LDL. The multi-well plate was covered with aluminum foil and incubated at 37° C. with gentle shaking for 4 h. Following incubation, samples were washed five times with PBS buffer, fixed in cold phosphate-buffered 4% paraformaldehyde for 48 h, embedded in paraffin, and sectioned at 5 µm thickness. Following de-paraffinization and DAPI staining, slides were examined using a fluorescence microscope (Olympus FSX100).

BODIPY-surfactant uptake. To assess the viability and functional uptake of type II pneumocytes, fluorescent BODIPY-labelled surfactant protein B (BODIPY-SPB) was delivered into the distal lung using a Renegade microcatheter system (Boston Scientific) and a flexible bronchoscope. After 30 min, a surgical stapler with medium/thick reloads (Triple-Staple Technology; Medtronic) was used to collect lung samples. Samples were dissected, rinsed in DPBS buffer, and imaged immediately with an Olympus FSX100 microscope. Enhanced resolution was obtained by incubating 36 h lung tissue specimens (2 mm×2 mm) with 20 ng ml$^{-1}$ BODIPY-SPB for 30 min at room temperature. Specimens were stained with CellMask Deep Red plasma-membrane stain for 10 min, followed by five washings with DPBS for 1 min each. Images were taken with a two-photon confocal laser scanning microscope (Leica TCS SP8). Visualization of the fluorescence signal in a speculated pattern (lamellar bodies) within type II pneumocytes indicated surfactant uptake.

Vasoconstriction/responsiveness test. The effect of catecholamine stimulation on pulmonary vascular tone was tested after 36 h of cross-circulation. Epinephrine (4 mg; International Medication Systems) was intravenously administered into the PA cannula of the extracorporeal lung. PA and PV pressure and flow were continuously recorded, as previously described, to assess the changes in pulmonary artery and vein pressures (and thus the trans-pulmonary pressure gradient) in response to the adrenoceptor-mediated effect of epinephrine.

Recipient haemodynamic and physiologic monitoring continued throughout the duration of study. To confirm that the response was isolated to the lung and not affected by haemodynamic changes in the recipient, the test was repeated with the lung decoupled from cross-circulation while on isolated EVLP.

Metabolic activity assay. To assess changes in lung metabolism, lung tissue from randomly selected wedge samples was collected after 0, 18 and 36 h of cross-circulation. Parenchymal samples (approximately 250 µl in volume; n=6) were dissected in a sterile fashion, finely minced, gently homogenized and placed in a 96-well plate. AlamarBlue assay (Thermo Fisher) reagent was diluted 1:10 in DMEM cell culture media with 10% foetal bovine serum, and 100 µl of AlamarBlue was added to wells containing lung sample homogenates. AlamarBlue alone (100 µl) was added to wells containing no lung homogenate (negative controls).

The multi-well plate was covered with aluminum foil and incubated at 37° C. with gentle shaking for 2 h. Following incubation, well contents were transferred into new 96-well plates, and absorbance was measured at 570 nm and normalized to 600 nm. Following the metabolic activity assay, the DNA content of each sample was quantified using Quanti-iT PicoGreen dsDNA Assay kit (Invitrogen) according to the manufacturer's instructions. Samples were digested in 250 µg ml$^{-1}$ papain at 60° C. for 4 h and mixed with PicoGreen reagent. Fluorescence emission was measured at 520 nm with excitation at 480 nm, and DNA was quantified using a standard curve.

Myeloperoxidase activity assay. To study the activity of myeloperoxidase, a peroxidase enzyme most abundant in neutrophil granulocytes, lung tissue samples were collected at multiple time points throughout the cross-circulation procedure. Small tissue sections (≥10 mg) were immediately snap frozen in liquid nitrogen and stored at −80° C. Once all time point samples were collected, the assay was conducted according to the manufacturer's instructions (Abcam, ab111749).

Live cilia imaging. To visualize the presence of cilia and assess their function, large airway sections were collected following 36 h of cross-circulation. Specimens were dissected into small pieces (2 mm×2 mm) and placed lumen-side-down onto a 50 mm glass-bottom dish (MatTek). Tissue was immersed in a 1:100 microbead (0.2 µm) suspension in PBS. A SecureSlip coverslip (Grace Bio-Labs) was placed on top of the sample. Remaining suspension outside the area of the coverslide was gently aspirated using a pipette. Images were acquired using an inverted Olympus IX81 microscope with an Andor Zyla 5.5 sCMOS camera at 100 frames·s$^{-1}$ and NIS Elements Advanced Research software (Nikon). The methods were adapted from previously described imaging techniques in rodents.

Immunohistochemical Staining.

Lung sections were de-paraffinized, subjected to boiling citrate buffer (pH 6.0) for antigen retrieval and blocked with 10% normal goat serum in PBS for 2 h at room temperature. Primary antibodies were added and incubated for 12 h at 4° C. or 4 h at room temperature. For all stains, the secondary antibody was diluted 1:200 and incubated for 1 h at room temperature. Sections were mounted in Vectashield Mounting Medium with DAPI (Vector Laboratories), coverslipped, and imaged with an Olympus FSX100 microscope. Late apoptosis was detected on tissue sections using a TUNEL (TdT-mediated dUTP nick end-labelling) assay. Additional stains for neutrophil elastase, pan-cytokeratin, caspase-3, CD163 and CD31 were conducted by the Herbert Irving Comprehensive Cancer Center molecular pathology services at Columbia University.

Histopathologic Analysis.

Sample collection. Before starting the experiment, the location of each lung wedge sample was randomized for each time point. The lung was divided into 16 regions, and a random number generator (http://www.random.org) was used to assign a lung region to each sample collection time point to avoid sampling bias. A surgical stapler with medium/thick reloads was used to obtain lung samples every 4 h. Specimens were immediately fixed in cold phosphate-buffered 4% paraformaldehyde for 48-72 h, embedded in paraffin, and sectioned at 3 µm or 5 µm thickness. All sections were stained for H&E and examined via light microscopy. Additional sections were stained for silver reticulin, Alcian blue (pH 2), elastic van Gieson, trichrome and pentachrome by the histology service of the Department of Molecular Pathology at Columbia University.

Blinded pathologic review. A pulmonary pathologist blinded to the study protocol and experimental groups evaluated slides (H&E and immunohistochemical staining for neutrophil elastase, TUNEL and caspase-3) from the 0, 12 and 24 h timepoints of all cross-circulation experiments (prolonged maintenance, ischaemia trials and ischaemic recovery). All slides were randomized, arbitrarily numbered and delivered to the pathologist without reference to experimental time points or conditions. To evaluate the extracorporeal lung at each time point, a modified lung injury score was developed from previously described methods. Scoring was based on alveolar oedema (0⇒<5% of all alveoli had oedema fluid, 1⇒6-25%, 2⇒26-50%, 3⇒>50%), interstitial infiltrate (lymphocytes and neutrophils in the interstitium around vessels and airways and in alveolar septa and pleura (1⇒<50 per high-power field (hpf), 2⇒50-100 per hpf, 3⇒>100 perhpf), neutrophilsper 5 hpf (×40; 0.2 mm$^2$; 0⇒<5, 1⇒6-10, 2⇒11-20, 3⇒>20), and total number of apoptotic cells per 5 hpf (×40; 0.2 mm$^2$; 0⇒<2, 1⇒3-5, 2⇒6-10, 3⇒>10). Numbers for early and late apoptosis, as quantified by caspase-3 and TUNEL, were combined into a single score. The sum of individual scores yielded a total lung injury score ranging from 0 to 12 as an index of lung maintenance and injury at each experimental time point.

Imaging

Thermal images of the lung were captured at selected time points throughout the duration of study using a Seek Thermal XR camera or a FLIR T430sc infrared camera. Continuous time-lapse photography (1 frame min) was performed using a Hero4 Black 4K camera (GoPro).

Electron Microscopy.

Scanning electron microscopy. Lung samples obtained at cross-circulation times of 0 and 36 h were fixed in formalin, rinsed in 70% ethanol, frozen and lyophilized. Airway castings were obtained at 36 h using a commercially available anatomical corrosion kit (Batson's #17, Polysciences) according to the manufacturer's instructions. Sections were imaged on a Hitachi S-4700 FE-SEM or a Zeiss Gemini SEM 300 with an accelerating voltage of 2.5 kV.

Transmission electron microscopy. Lung samples obtained at cross-circulation times of 0 and 36 h were fixed with 2.5% glutaraldehyde in 0.1 M Sorenson's buffer (pH 7.2). Samples were then post-fixed with 1% $OsO_4$ in Sorenson's buffer for 1 h. After dehydration, tissues were embedded in Lx-112 (Ladd Research Industries). Thin sections were cut on the PT-XL ultramicrotome at 60 nm thickness. The sections were stained with uranyl acetate and lead citrate and examined under a JEOL JEM-1200 EXIT electron microscope. Images were captured with an ORCA-HR digital camera (Hamamatsu) and recorded using the AMT Image Capture Engine v.602.569.

Therapeutic Delivery into Extracorporeal Lung.

Decellularization of target lung regions. Decellularization of target lung regions (removal of lung epithelium, with endothelial preservation) was accomplished by delivering decellularization solution through the airway. A mild detergent solution containing 8 mM CHAPS (Sigma), 0.5 M NaCl (Sigma) and 25 mM EDTA (Sigma) was introduced bronchoscopically into targeted bronchopulmonary segments by a custom micro-catheter delivery system. Immediately following withdrawal of the bronchoscope, a 4-7F Fogarty occlusion catheter (Edwards Lifesciences) was inflated and left in place to prevent escape of decellularization fluid from the targeted region. Decellularization solution was allowed to dwell for 4 h before repeated bronchoalveolar lavage with sterile normal saline. To assess the effectiveness of decellularization, lung wedge samples were collected following decellularization and before further intervention, fixed, embedded, de-paraffinized, and imaged, as previously described.

Delivery of mesenchymal stem cells. Porcine adipose-derived MSCs were isolated from three different donor animals (mature Yucatan mini-pigs; 21-32 months old; 48-73 kg or a mean of 60.0±7.9 kg). Subcutaneous fat (about 20 g) was collected from the dorsal abdominal area of each animal (n=3), and the adipose-derived stem cells were isolated as previously described[58]. MSCs were cultured in DMEM, 10% foetal bovine serum, 1% penicillin/streptomycin and 0.1 ng ml$^{-1}$ basic fibroblast growth factor, and expanded up to passage 3 before use. At the time of the experiment, passage-3 cells were trypsinized, counted using a Countess automated cell counter (Invitrogen), and re-suspended in PBS at a final concentration of 3-30×10$^6$ cells ml$^{-1}$ for labelling with CSFE (Abcam) or CellBrite NIR790 cytoplasmic membrane dye (Biotium) according to the manufacturers' instructions.

Cell delivery was performed using a 3.8 mm flexible bronchoscope with a 1.2 mm lumen for therapeutic delivery and intervention. Labelled cells in suspensions of single-cell or 5-10 cell aggregates were delivered either globally (from above the carina) or locally into targeted lobes or segments. For single-cell delivery, cells were delivered within 15 min of suspension and gentle rocking was maintained prior to delivery. For 5-10 cell aggregates, cells were allowed to settle without rocking for up to 30 min, delivery was completed once aggregates were confirmed by microscopy. Timing of MSC delivery was varied experimentally (at 20, 24 or 26 h of cross-circulation). Subsequent live transpleural imaging of near-infrared-labelled cells was performed using a custom imaging system developed in our lab that consists of an LED excitation source (M780L3, Thorlabs), a camera (Zyla 4.2, Andor Technology) and an objective (Plan N 10×, Olympus). Images and videos acquired with the system were processed using MS-Elements Advanced Research or ImageJ v.1.43u (National Institutes of Health). To assess the distribution, attachment and migration of CSFE-labelled MSCs, lung wedge samples were collected from all lobes at the end of the experiment, fixed, embedded, de-paraffinized and imaged as previously described, using an Olympus BX61VS virtual slide microscope.

Delivery of CSFE and fluorescent microbeads. To demonstrate the feasibility of targeted delivery of fluid microvolumes into the distal lung, CFSE (Affymetrix, eBioscience) was reconstituted in dimethyl sulfoxide at a concentration of 1.06 M and protected from light. Fluorescent microbeads (FluoSpheres F-8834, Life Technologies; excitation/emission, 580/605 nm; diameter, 10 µm) were suspended in PBS at a final concentration of $10^6$ beads $ml^{-1}$. At determined experimental time points, either CFSE or microbeads were delivered into the airways with a flexible bronchoscope and Renegade microcatheter system. Following delivery, microbeads were imaged transpleurally using the imaging system described above, using a 595 nm LED (M595L3, Thorlabs) as the excitation source. To assess the distribution and uptake of CSFE, lung wedge samples were collected at the end of the experiment, fixed, embedded, de-paraffinized and imaged, as previously described.

Delivery of human airway epithelial cells and human embryonic stem cell-derived alveolar progenitor cells. Following decellularization, shake tests of BAL fluids were conducted to confirm the removal of residual detergent before the introduction of cells. Human airway epithelial cells (Lonza, Allendale) or human embryonic stem cell-derived alveolar progenitor cells (derived from Rockefeller University Embryonic Stem Cell Line 2; NIH approval number, NIHhESC-09-0013; registration number, 0013; passage 13-24; negative for mycoplasma) were cultured as previously described. Cultured cells were passaged by trypsinization, labelled with CFSE according to the manufacturer's instructions, and suspensions were prepared at a concentration of $5\text{-}10\times10^6$ cells $ml^{-1}$. Cells were then suspended in a lung-specific extracellular matrix hydrogel (TissueSpec Matrix Hydrogel; MatriTek) and delivered either proximally to decellularized airways or distally to decellularized regions of the respiratory zone. Delivery of cells occurred after 24 h of cross-circulation to allow sufficient time for cell distribution and attachment. To assess the distribution and attachment of delivered cells, lung wedge samples were collected at the conclusion of the experiment, fixed, embedded, de-paraffinized, and imaged, as previously described.

Statistical Analysis.

One-way analysis of variance test with Tukey's multiple comparison post hoc tests and Student's t-tests were performed using Prism v.6 (GraphPad). A value of $p<0.05$ was considered statistically significant.

Having described and illustrated the principles of our invention with reference to the described embodiments, it will be recognized that the described embodiments can be modified in arrangement and detail without departing from such principles. It should be understood that the systems, processes, or methods described herein are not related or limited to any particular type of environment, unless indicated otherwise.

In view of the many possible embodiments to which the principles of our invention can be applied, we claim as our invention all such embodiments as can come within the scope and spirit of the following claims and equivalents thereto.

What is claimed is:

1. A system for maintaining an extracorporeal organ, tissue or bioengineered graft, comprising
    an extracorporeal chamber to contain and support the organ, tissue or bioengineered graft; wherein the chamber comprises a time- and temperature-controlled humidifier and misting spray onto the organ, tissue or bioengineered graft and into the chamber to maintain a humid environment within the chamber; and
    an extracorporeal cross-circulation circuit to connect the organ, tissue or bioengineered graft with a host organism for cross-circulation of blood or plasma, comprising
        fluid conduits providing flow of the blood or plasma between a vascular system of the host organism to vasculature of the organ, tissue or bioengineered graft
        an arterial pressure sensor for sensing extracorporeal in-flow line pressure;
        a venous pressure sensor for sensing extracorporeal out-flow line pressure; and
        a controller configured to control a circulating pump to regulate blood or plasma flow within a range of 5% to 10% of cardiac output of the host organism based on the trans-organ pressure difference between arterial and venous pressure measured by the arterial pressure sensor and the venous pressure sensor.

2. The system of claim 1 wherein the extracorporeal organ chamber comprises
    an organ- and size-specific organ-negative molded soft bladder for supporting the organ, tissue or graft, and
    a water circulating loop in the interior of the soft bladder for continuously recirculating water from a temperature-controlled reservoir by a pump to provide a temperature-controlled interior of the bladder maintained with recirculating temperature-controlled water in a range from 4° C. to 40° C.

3. The system of claim 2 wherein the chamber further comprises one or more of the following features including integrated scale for monitoring and recording organ weight, real-time macroscopic video recording of the organ with remote monitoring capability, access ports with sterile air filter for biopsies and/or imaging, access for sterile manual interventions in chamber, and sterilizable and single-use disposable components.

4. The system of claim 1 wherein the extracorporeal cross-circulation circuit further comprises one or more of the following features including a re-circulation tubing jacket for warming exposed tubing, integrated heat exchanger, integrated access ports for blood sampling, and remote monitoring and control of the circulating pump.

5. The system of claim 1 further comprising an extracorporeal organ chamber stand comprising
    automatic height adjustability based on feedback from extracorporeal organ in-flow and out-flow line pressures; wherein the organ chamber stand includes the ability to raise and lower the organ chamber to modulate cross-circulation circuit pressures so that desirable perfusion rates are maintained;
    optionally at least one organ-specific accessory; and
    a power source.

6. The system of claim 1, wherein the organ is a lung.

7. The system of claim 6, wherein the circulating pump is configured to maintain the trans-organ blood pressure difference to between about 5-15 mm Hg.

8. The system of claim 1, wherein the extracorporeal cross-circulation circuit comprises an additional extracorporeal circuit containing a filter that permits return of blood cells directly to the host organism and perfusion of plasma through the extracorporeal organ.

9. The system of claim 1, wherein the extracorporeal cross-circulation circuit is configured for cross-circulation of plasma and further comprises at least one of the following:
- a filter (PF) configured to permit return of blood cells directly to the host organism and perfusion of plasma through the organ, tissue or bioengineered graft; and
- a leukocyte reduction filter (L) configured to prevent immunologic cells exiting the organ, tissue or bioengineered graft from entering the vascular system of the host organism.

* * * * *